United States Patent [19]

Weber

[11] Patent Number: 4,709,701

[45] Date of Patent: Dec. 1, 1987

[54] APPARATUS FOR MEDICAL TREATMENT BY HYPERTHERMIA

[75] Inventor: Raviv Weber, Herzliya, Israel

[73] Assignee: Medical Research & Development Associates, Potomac, Md.

[21] Appl. No.: 851,724

[22] Filed: Apr. 14, 1986

[51] Int. Cl.$^4$ ............................................. A61N 1/40
[52] U.S. Cl. .................................. 128/422; 128/804; 219/10.77
[58] Field of Search ..................... 128/804, 421, 422; 219/10.77

[56] References Cited

U.S. PATENT DOCUMENTS

| | | | |
|---|---|---|---|
| 2,415,799 | 2/1947 | Reifel et al. | 128/422 |
| 2,752,496 | 6/1956 | Martens | 128/422 |
| 3,543,762 | 12/1970 | Kendall | 128/422 |
| 4,210,152 | 7/1980 | Berry | 128/422 |

FOREIGN PATENT DOCUMENTS

| | | | |
|---|---|---|---|
| 0136363 | 4/1985 | European Pat. Off. | 128/422 |
| 759038 | 10/1956 | United Kingdom | 128/422 |
| 2126098 | 3/1984 | United Kingdom | 128/421 |

Primary Examiner—Lee S. Cohen
Attorney, Agent, or Firm—Weingarten, Schurgin, Gagnebin & Hayes

[57] ABSTRACT

Hyperthermia apparatus including a power amplifier, remote electrode apparatus receiving a high power electrical supply from the power amplifier, power transmission apparatus arranged to electrically couple the power amplifier to the remote electrode apparatus for supply of electrical power thereto and capacitive matching apparatus for providing real time capacitive matching between the power amplifier and the capacitive load across the electrode apparatus.

2 Claims, 17 Drawing Figures

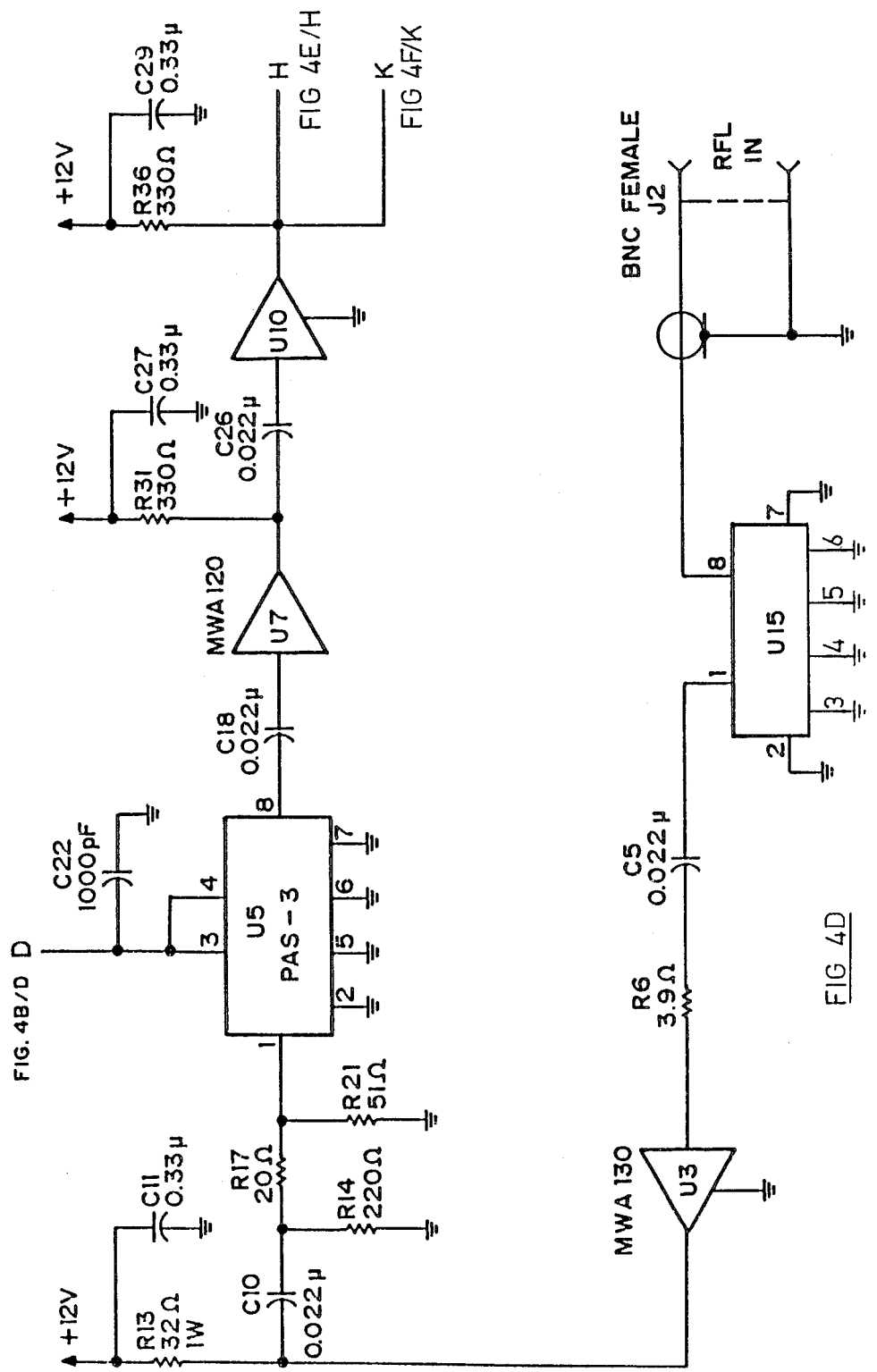

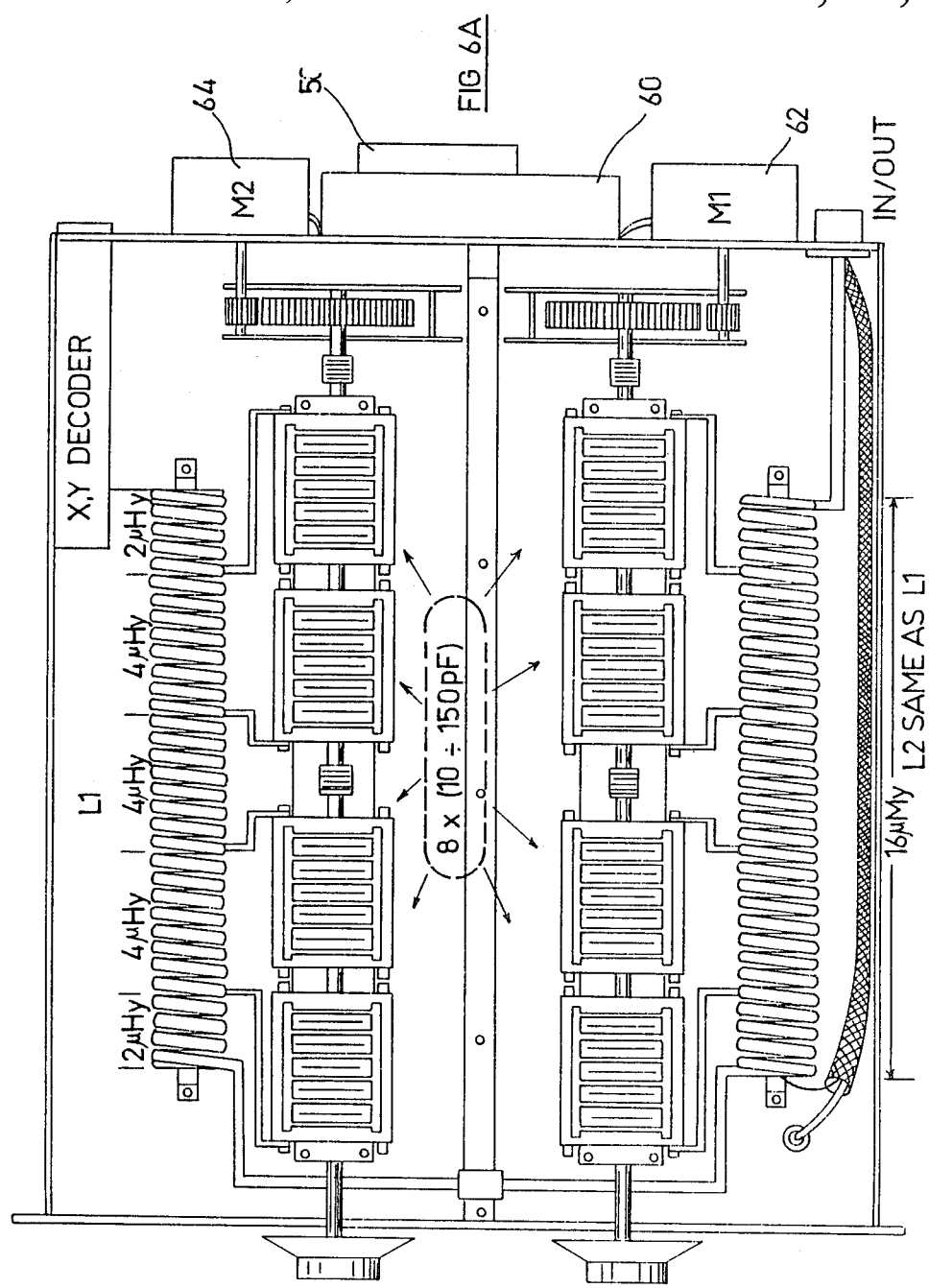

APPARATUS FOR MEDICAL TREATMENT BY HYPERTHERMIA

FIELD OF THE INVENTION

The present invention relates to apparatus for medical treatment by hyperthermia generally and specifically to apparatus for capacitive matching between a power amplifier and a capacitive load along a power transmission line in such apparatus.

BACKGROUND OF THE INVENTION

The use of hyperthermia in treatment of malignant tumors is well known and documented. A summary report reflecting the state of the art in 1982 appears in the following publication:

Manning, M. R., T. C. Cetas, R. C. Miller, J. R. Oleson, W. G. Connort, and E. W. Gerner, "Clinical Hyperthermia, Results of a Phase I Trial Employing Hyperthermia Alone or in Combination with External Beam or Interstitial Radiotherapy," Cancer Vol. 49, pp. 205-216, 1982.

One type of hyperthermia treatment employs capacitive heating of the tumor by means of a pair of electrodes placed on opposite sides thereof. Because significant amounts of electrical energy are involved, the problem of capacitive matching between the power amplifier and the capacitive load arises. As is well known, absence of good capacitive matching in a system causes a relatively large amount of wasted reflected power, thus requiring a much larger power amplifier than would otherwise be necessary, unwanted heating of the electrodes resulting in heat damage to the skin and subcutaneous layers of the patient's body.

In hyperthermia applications, it has been found by the inventors that adjustments in the capacitive matching should be made continually, in response to even minor movements of the patient, even those occasioned by normal breathing. Adjustments in the capacitive matching must also be made in response to the output power supplied to the electrodes. Prior art apparatus does not enable adjustments in capacitive matching to be readily made.

SUMMARY OF THE INVENTION

The present invention seeks to provide a hyperthermia system having extremely efficient capacitive matching apparatus operative in real time.

There is thus provided in accordance with a preferred embodiment of the present invention hyperthermia apparatus including a power amplifier, remote electrode apparatus receiving a high power electrical supply from the power amplifier, power transmission apparatus arranged to electrically couple the power amplifier to the remote electrode apparatus for supply of electrical power thereto and capacitive matching apparatus for providing real time capacitive matching between the power amplifier and the capacitive load across the electrode apparatus.

Additionally in accordance with a preferred embodiment of the present invention, there is provided for use in hyperthermia apparatus including a power amplifier, remote electrode apparatus receiving a high power electrical supply from the power amplifier, and power transmission apparatus arranged to electrically couple the power amplifier to the remote electrode apparatus for supply of electrical power thereto, capacitive matching apparatus for providing real time capacitive matching between the power amplifier and the capacitive load across the electrode apparatus.

In accordance with a preferred embodiment of the present invention, the capacitive matching apparatus comprises a capacitive matching unit and step motor apparatus for driving the capacitive matching apparatus.

Additionally in accordance with a preferred embodiment of the present invention there is provided control apparatus for governing the operation of the step motor apparatus in accordance with real time sensing of reflected power.

Further in accordance with an embodiment of the present invention, the control apparatus comprises apparatus for calculating a vector function indicating required capacitance changes.

Additionally in accordance with an embodiment of the present invention, the control apparatus comprises apparatus for governing the operation of the step motor in accordance with a Smith chart plot.

Further in accordance with an embodiment of the present invention, the capacitive matching apparatus is operative for providing capacitive matching over a range of applied power extending from less than 10 W to at least 1.2 KW.

Additionally in accordance with an embodiment of the present invention, the control apparatus comprises a bidirectional coupler, a decoder receiving an input from the bidirectional coupler and providing x and y coordinate indications of reflected power, and a computer operated controller receiving the output of the decoder and providing operating instructions to the step motor apparatus in accordance with Smith chart coordinates.

BRIEF DESCRIPTION OF THE DRAWINGS

The present invention will be understood and appreciated more fully from the following detailed description taken in conjunction with the drawings in which:

FIGS. 4A, 4B, 4C, 4D, 4E and 4F together are a schematic illustration of the decoder forming part of the apparatus of FIG. 3;

FIGS. 6A and 6B are respective top and end view illustrations of a matching unit useful in the apparatus of FIG. 2.

DETAILED DESCRIPTION OF A PREFERRED EMBODIMENT

Figure 1:
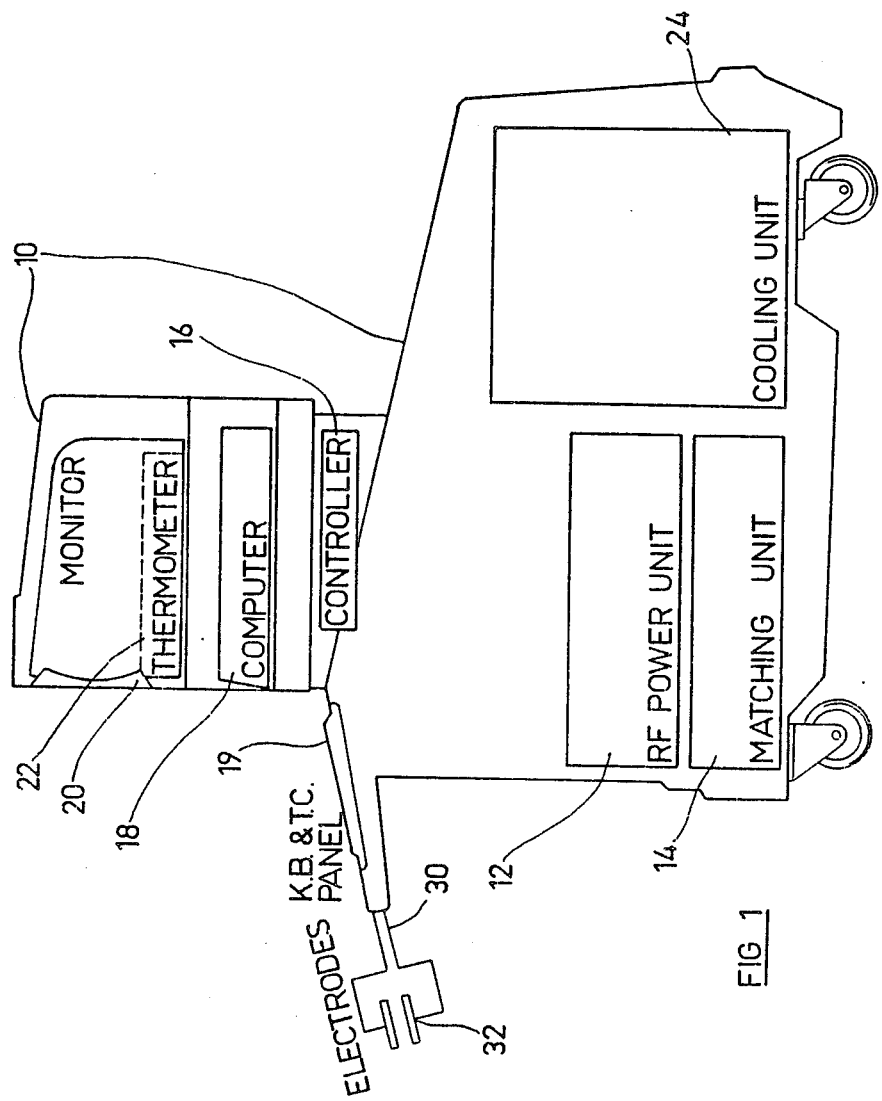
FIG. 1 is a partially pictorial, partially block-diagram illustration of hyperthermia apparatus constructed and operative in accordance with a preferred embodiment of the present invention.

Reference is now made to FIG. 1, which illustrates, in general form, hyperthermia apparatus constructed and operative in accordance with a preferred embodiment of the invention. The hyperthermia apparatus comprises a housing 10 which encloses a high frequency RF power unit 12, typically having a variable output power ranging from 0–1200 W, a high-frequency capacitance matching unit 14 coupled to RF power unit 12, a controller 16 operative in cooperation with the matching unit 14, a system computer 18, keyboard and control panel 19, display 20, thermometer 22 and cooling unit 24.

A power transmission line 30 provides electrical power from RF power unit 12 via capacitance matching unit 14 to electrodes 32, which are placed across a body region, portions of which are to be heated for treatment of tumors. Power deposition is accomplished through the interaction of electric fields produced by the electrodes in the tissues disposed therebetween. Surface cooling of the electrodes 32 is provided by cooling unit 24 via cooling fluid conduits (not shown) which also communicate with electrodes 32.

Briefly stated, the system illustrated in FIG. 1 and described hereinabove is operative to provide RF heating of selected tissue for tumor treatment. The capacitance matching unit is provided in order to minimize reflected power due to capacitance mismatching between the RF power unit 12 and the capacitive load across the electrodes 32. The computer 18, keyboard and control panel 19, and display 20, are operative to provide control and safety features for this operation as well as to provide data logging as desired.

Figure 2:
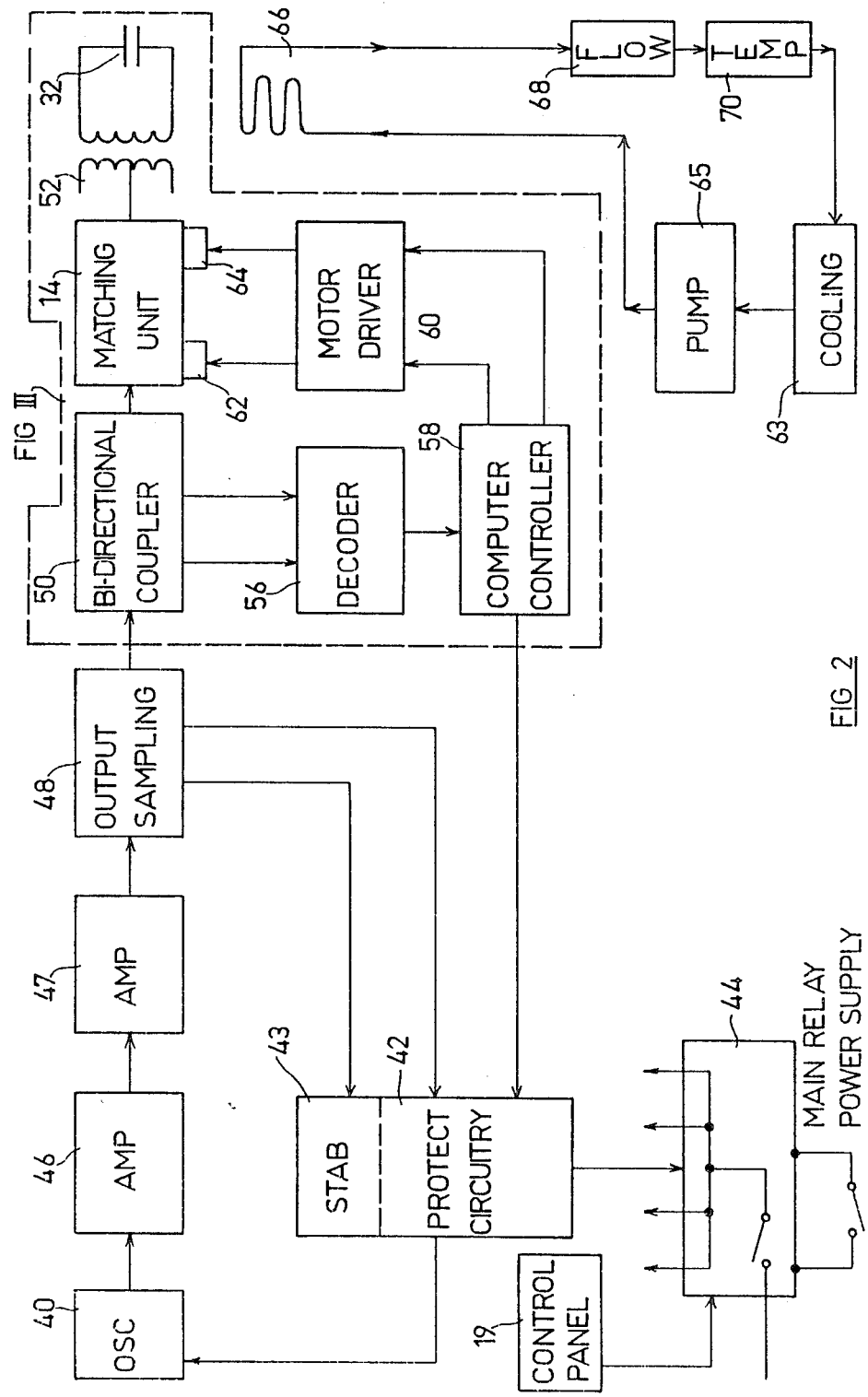
FIG. 2 is a functional block diagram illustration of a portion of the apparatus of FIG. 1.

Reference is now made to FIG. 2, which illustrates the basic structure of the HF capacitance matching unit 14 of FIG. 1. A high frequency oscillator 40, typically operating at 13.56 MHz, and having a variable power output, receives a control input from protection circuitry 42 which is operative to provide protection to the circuitry of FIG. 2 and to the patient from excessive incident and reflected power, cooling failure, and destabilization of the output power. The protection circuitry 42 also provides an output to switching circuitry 44, operated by an operator using control panel 19, to provide provide emergency power cut off.

The output of oscillator 40 is supplied first to a preamplifier 46 and then to a HF power amplifier 47, typically having a rating up to 1200 watts. An output sampling circuit 48 receives the output of amplifier 47 and supplies samples of the amplifier output back to protection circuitry 42 and to a stablilization circuitry 43 to stabilize the output power. The power output of amplifier 47 is provided via output sampling circuitry 48 to the capacitive matching apparatus, which is surrounded by dashed lines and is illustrated in more detail in FIG. 3.

It is noted that circuitries 40, 42, 43, 46, 47 and 48 are included in the RF power unit 12 (FIG. 1).

Considering FIG. 2 at this stage, it is seen that the capacitive matching apparatus comprises a bidirectional coupler 50 which receives the power output of RF power unit 12 and provides it via matching unit 14 (FIG. 1), and a suitable transformer 52, to the electrodes 32, across which is defined the capacitance of the patient's body.

It is extremely important to note that the capacitance of the patient's body varies over a relatively short time period, measurable in seconds, due to changes in body position, breathing and other anatomical variables. Accordingly, in accordance with the present invention, the matching unit 14 must be operated to provide adaptive capacitive management over the same general time period.

Bidirectional coupler 50 provides an output indication to a decoder 56 of both the transmitted and reflected power. Decoder 56 is operative to provide an indication of the vector coordinates in x-y coordinates, which represent the relationship of the reflected power to the transmitted power, to a computer controller 58. It has been found in practice that the representation of the relationship of the reflected power to the transmitted power in x-y coordinates is valid over a range of output power from about 10 W to 1200 W.

Computer controller 58 translates the information received from the decoder 56 into Smith chart form in accordance with the well-known teachings of P. H. Smith, which originally appeared in Smith, P. H., "Transmission-Line Calculator," Electronics, Vol. 12, pp. 29–31, January, 1939. An explanation of the Smith technique appears in *Engineering Electromagnetics*, International Student Edition, McGraw-Hill Kogakusha, Ltd. Tokyo, 1981 on pages 446–452.

Computer controller 58 provides an output in Smith chart coordinates to a motor driver 60 which, in turn, operates step motors 62, 64 of matching unit 14 in accordance with instructions received from computer controller 58 in order to immediately adjust the capacitive matching to changes in capacitance across electrodes 32.

Cooling apparatus comprising a cooling source 63, a pump 65, a cooling coil 66 associated with the electrodes 32, flow measuring apparatus 68 and temperature measuring apparatus 70, is also provided.

Figure 3:
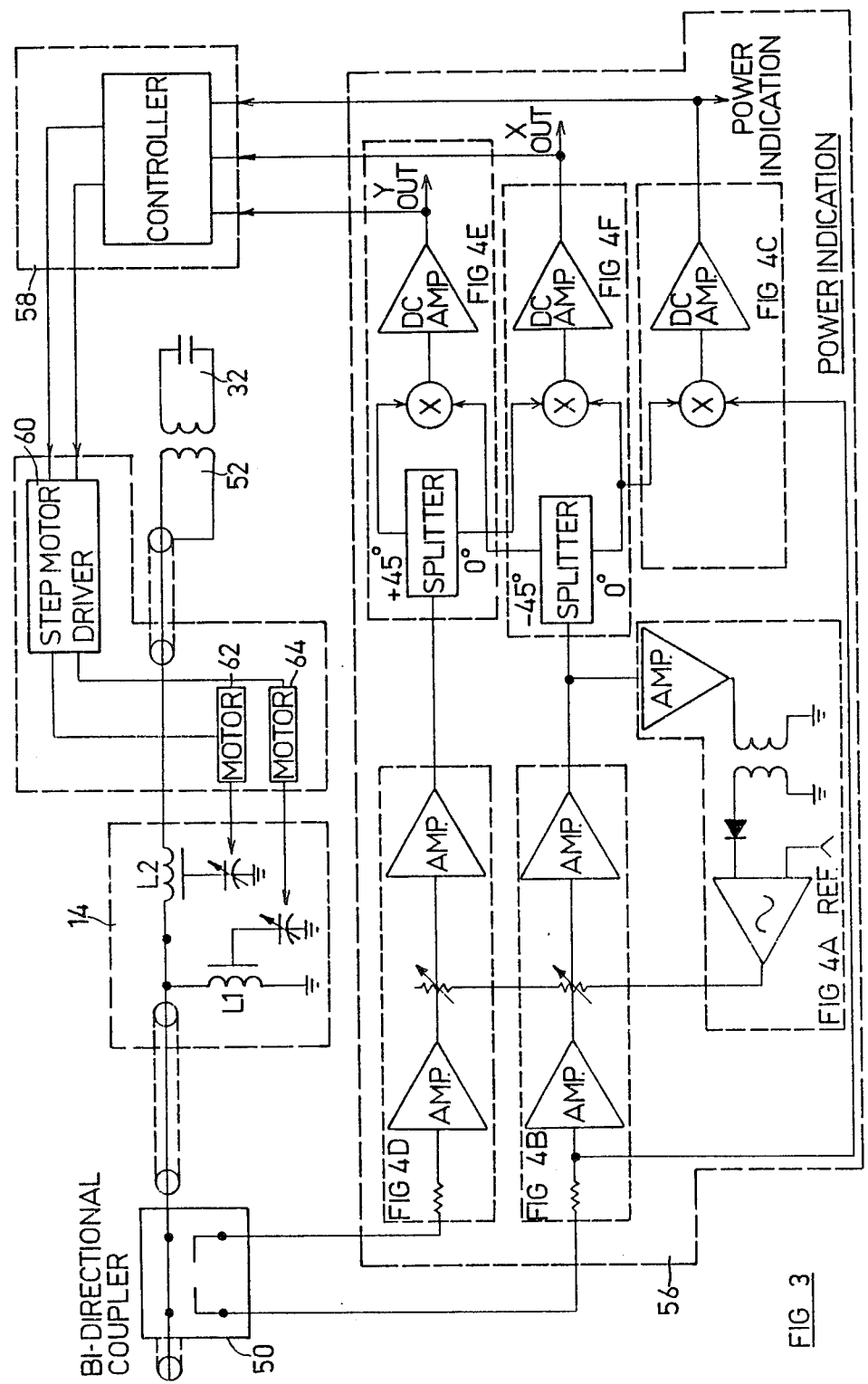
FIG. 3 is a partially schematic, partially block-diagram illustration of a portion of the circuitry of FIG. 2.
Figure 4A:
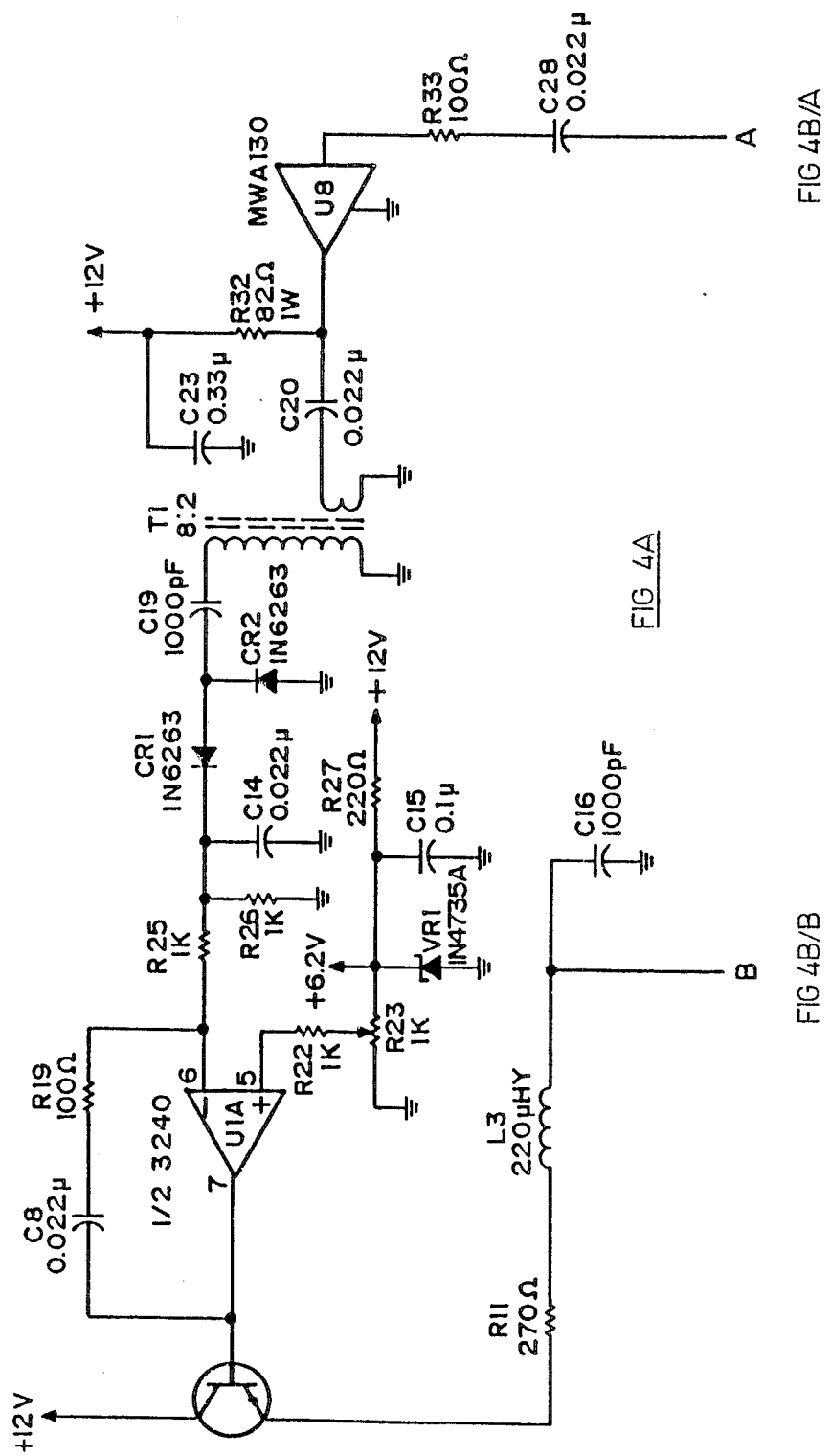
Figure 4B:
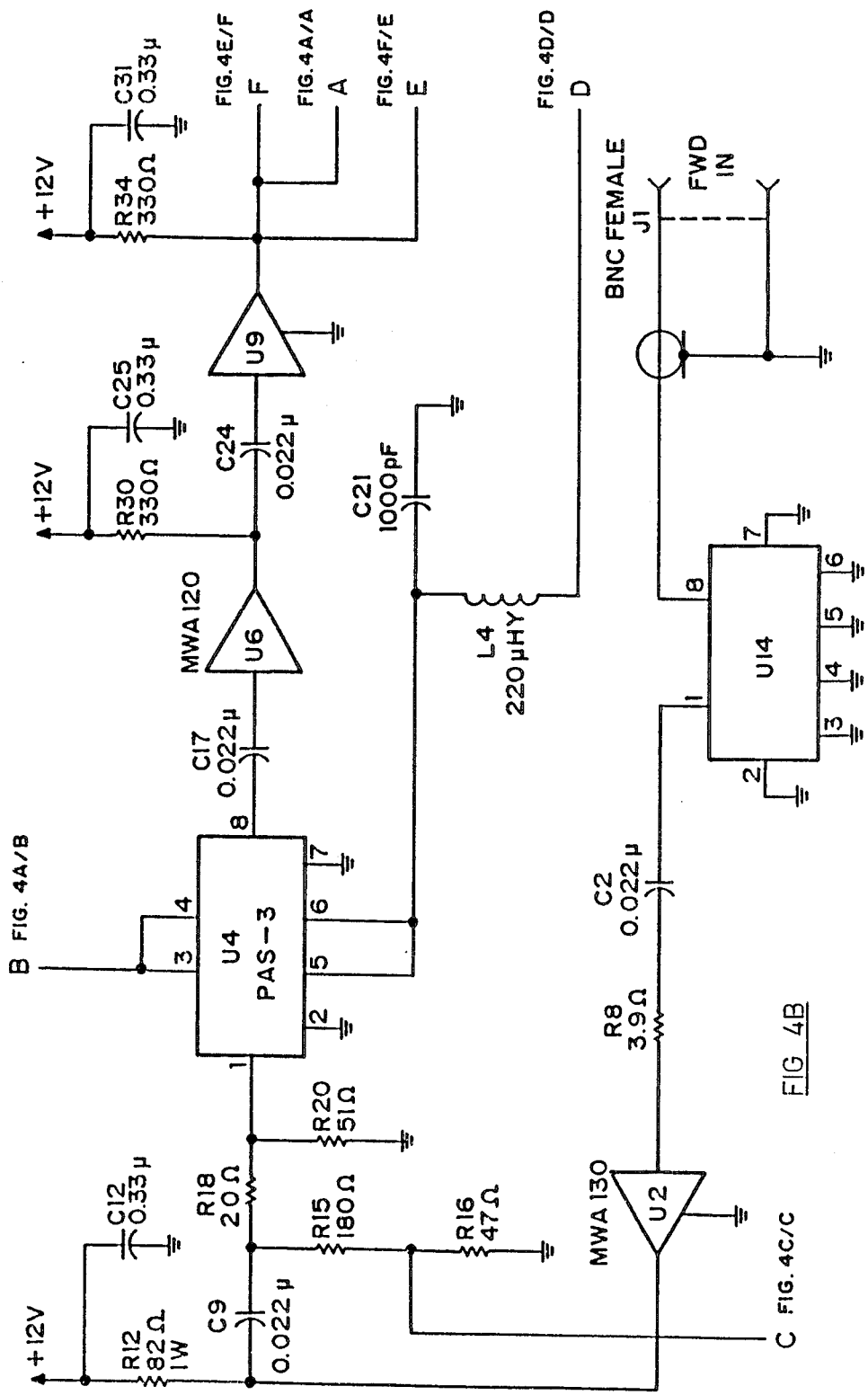
Figure 4C:
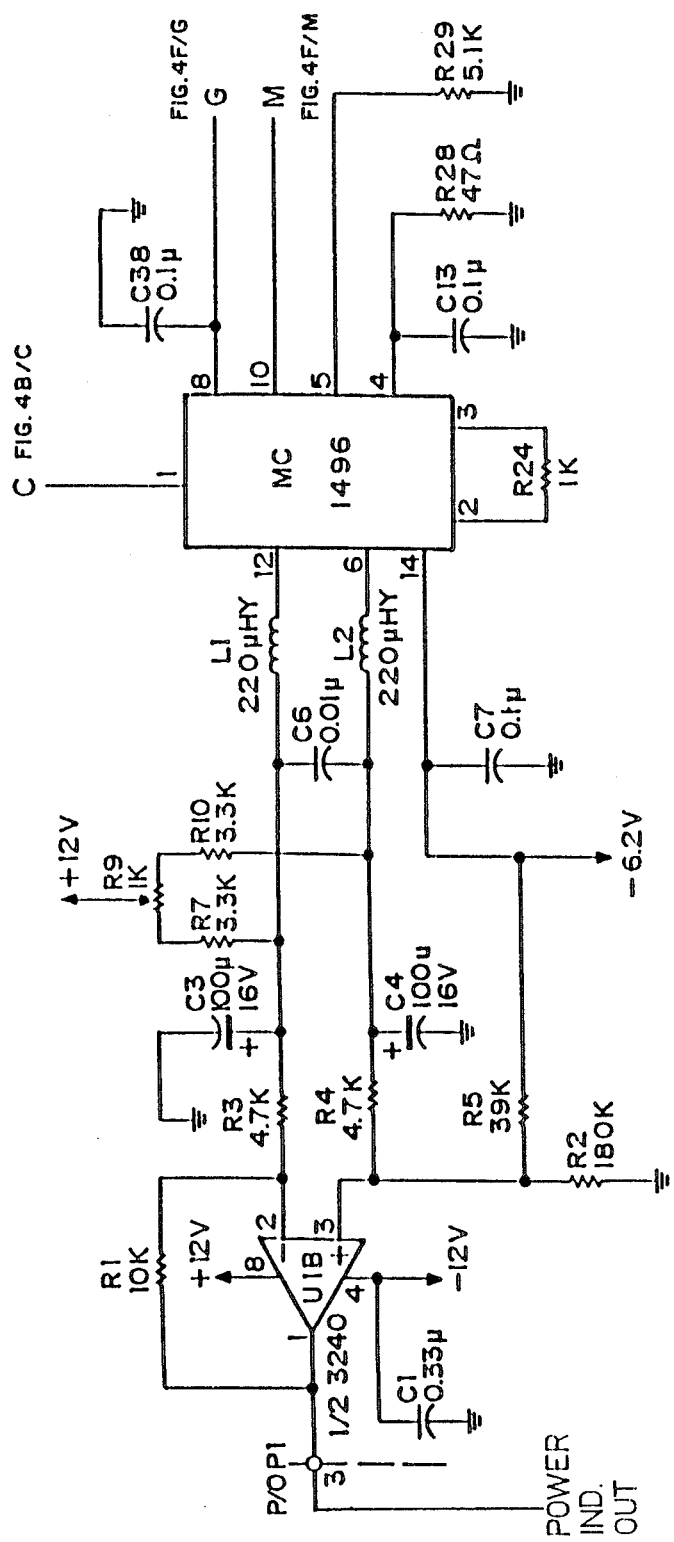
Figure 4E:
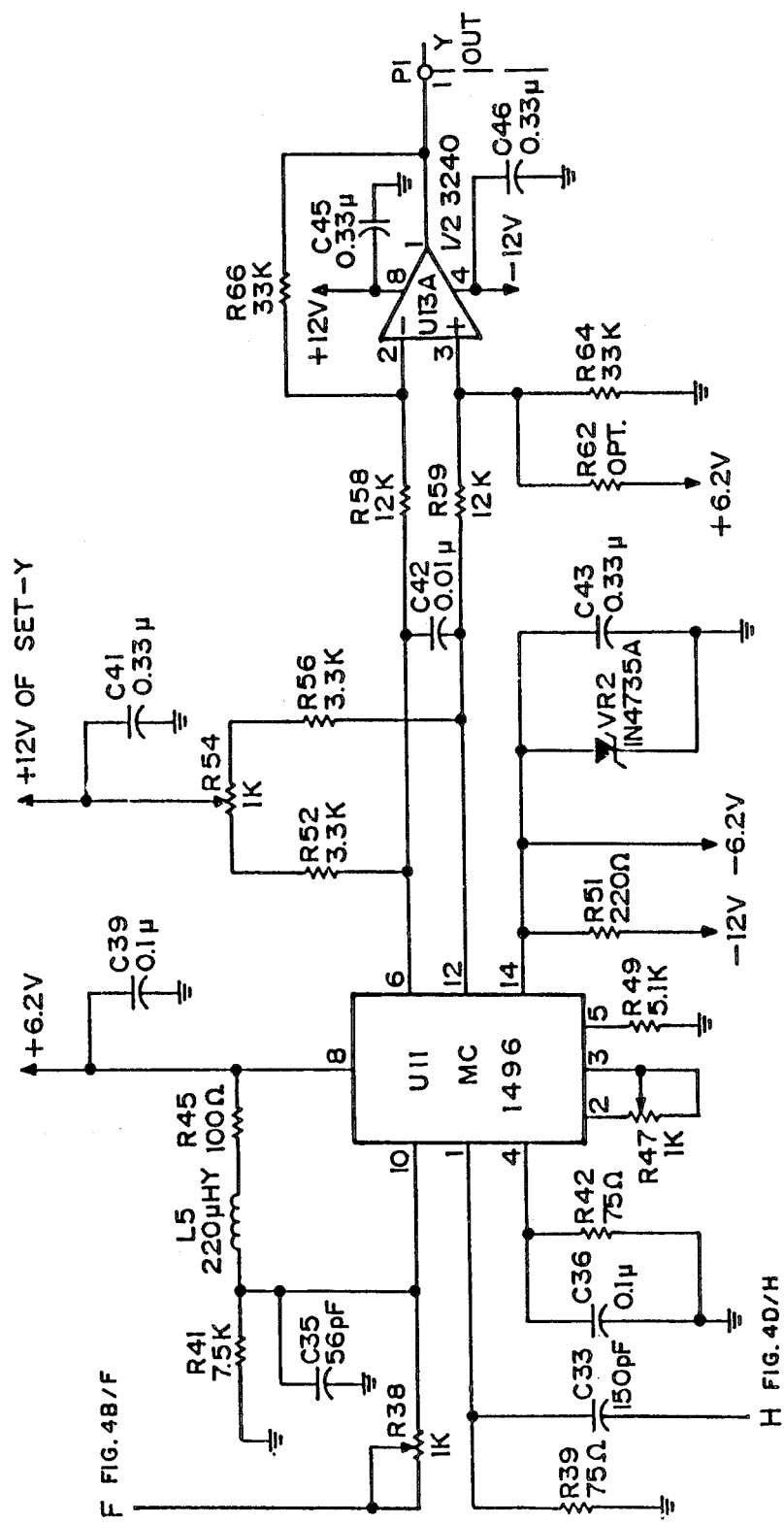
Figure 4F:
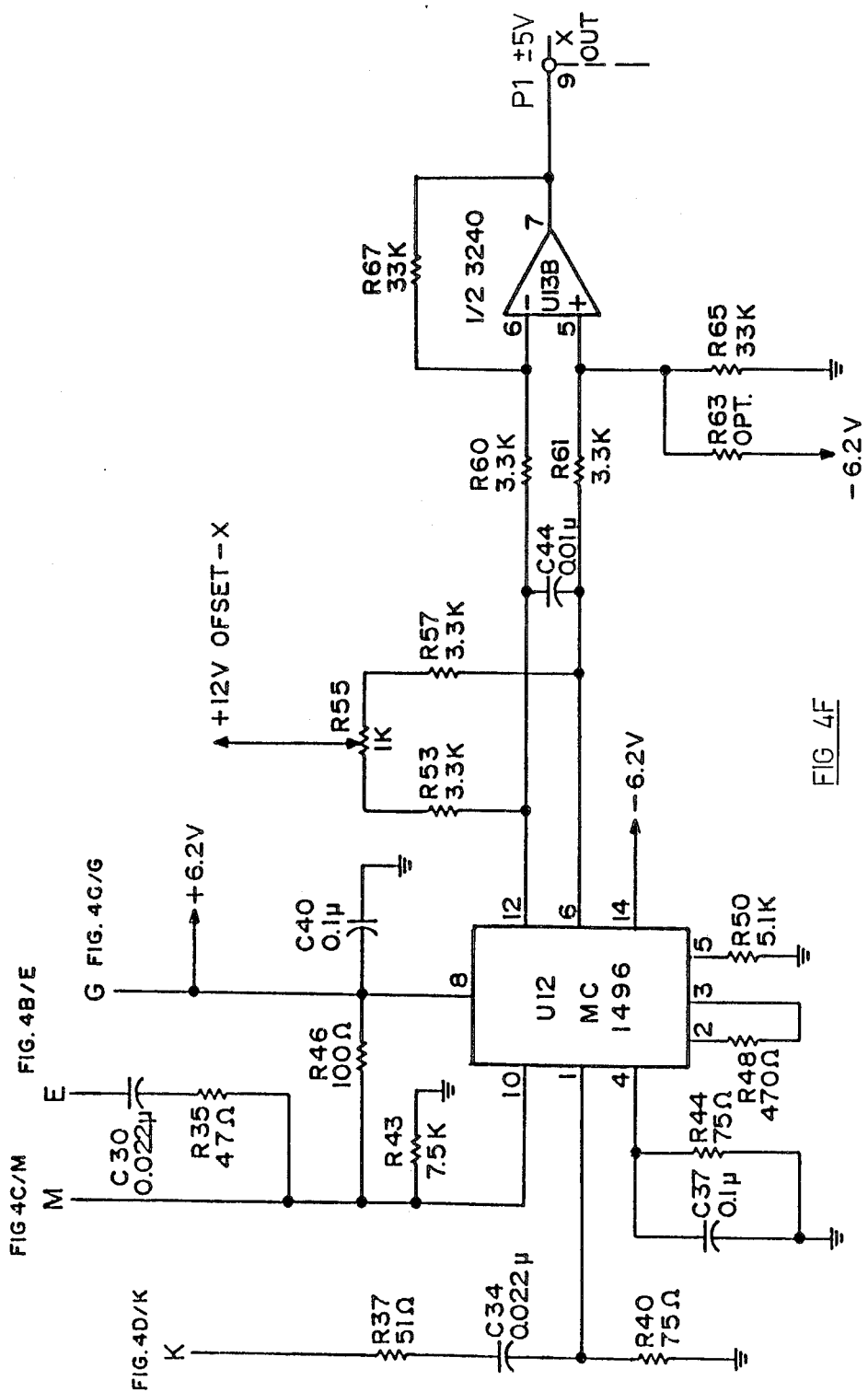
Figure 5A:
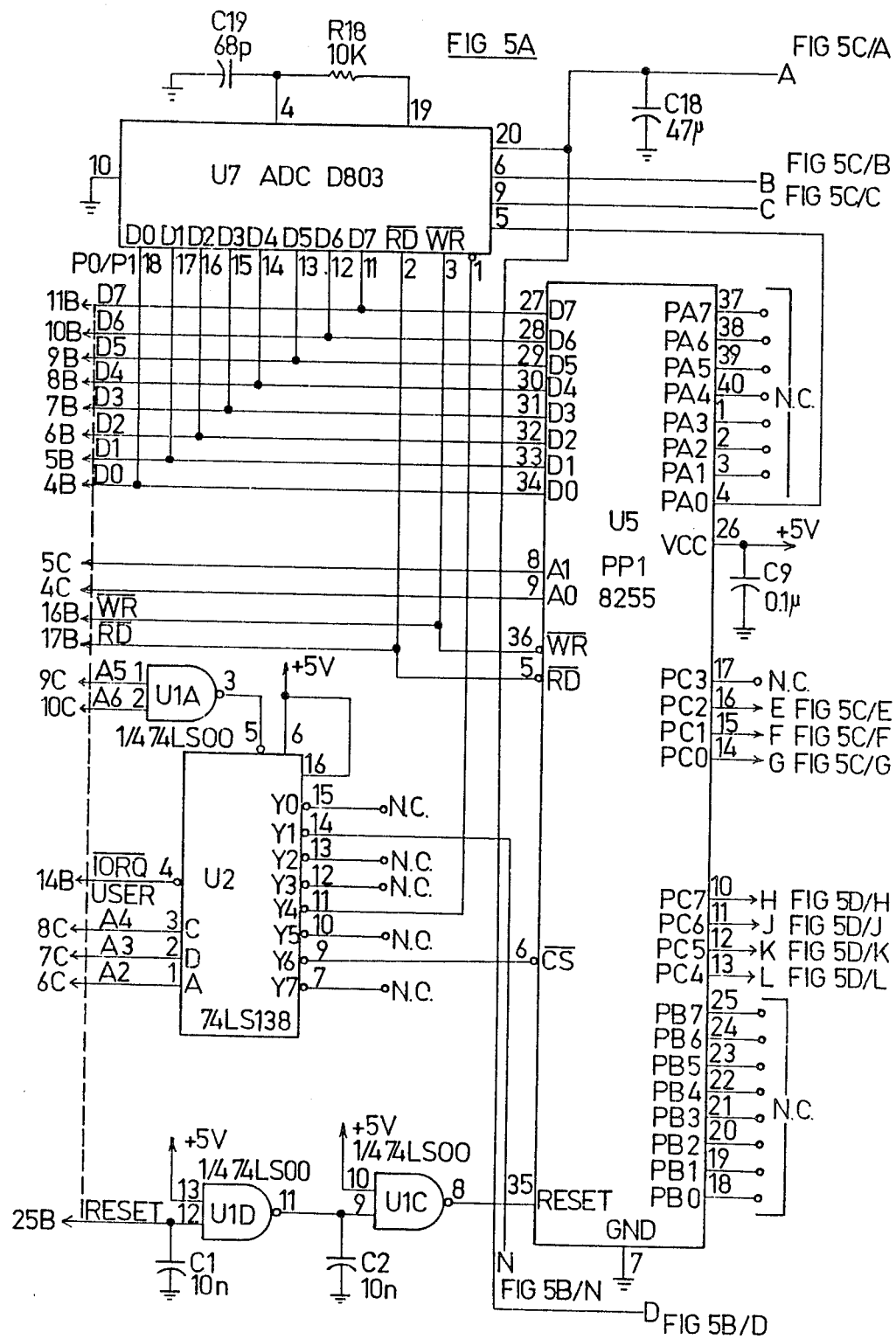
FIGS. 5A, 5B, 5C and 5D are together a schematic illustration of the computer controller forming part of the apparatus of FIG. 2 less the CPU associated therewith.
Figure 5B:
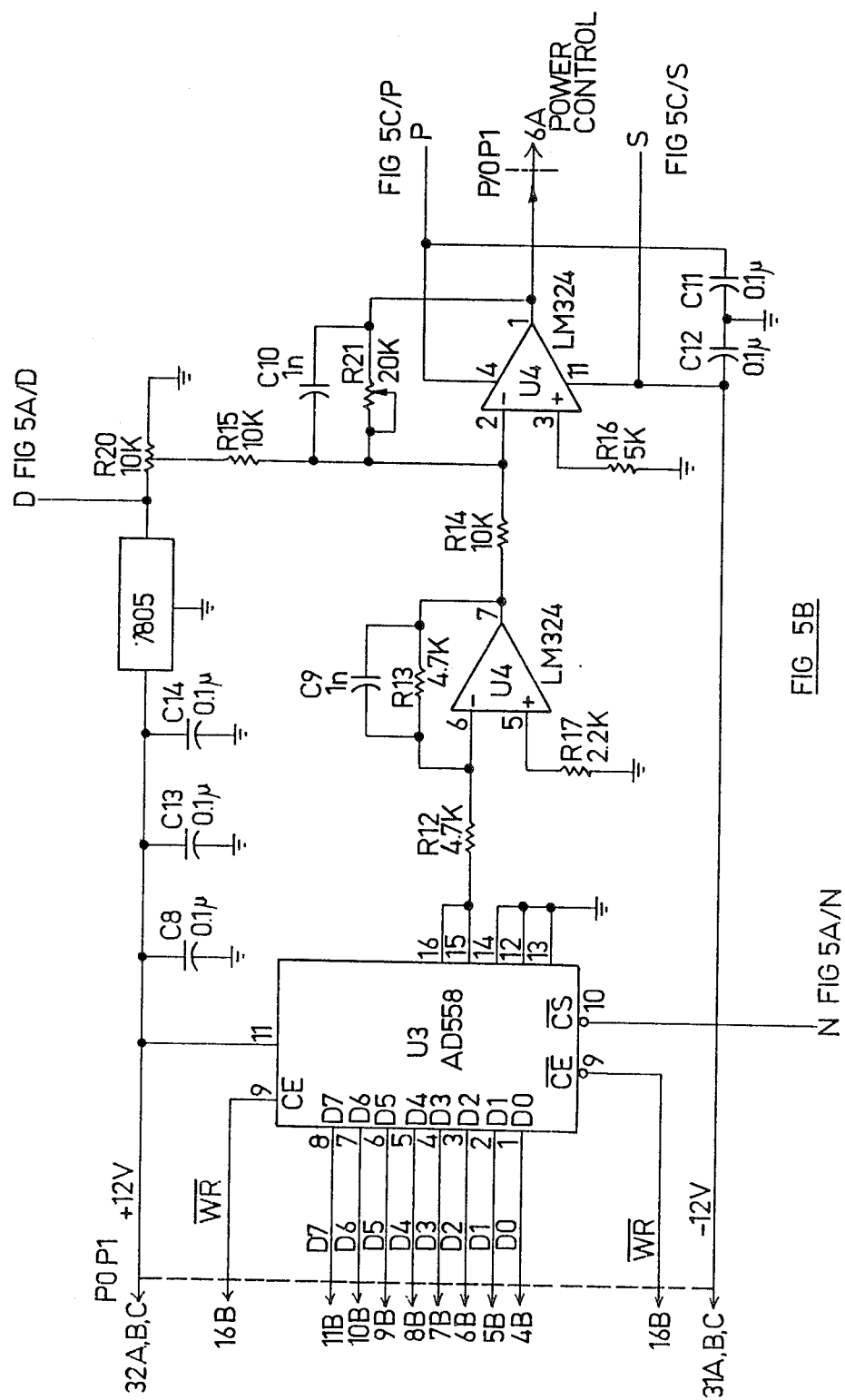
Figure 5C:
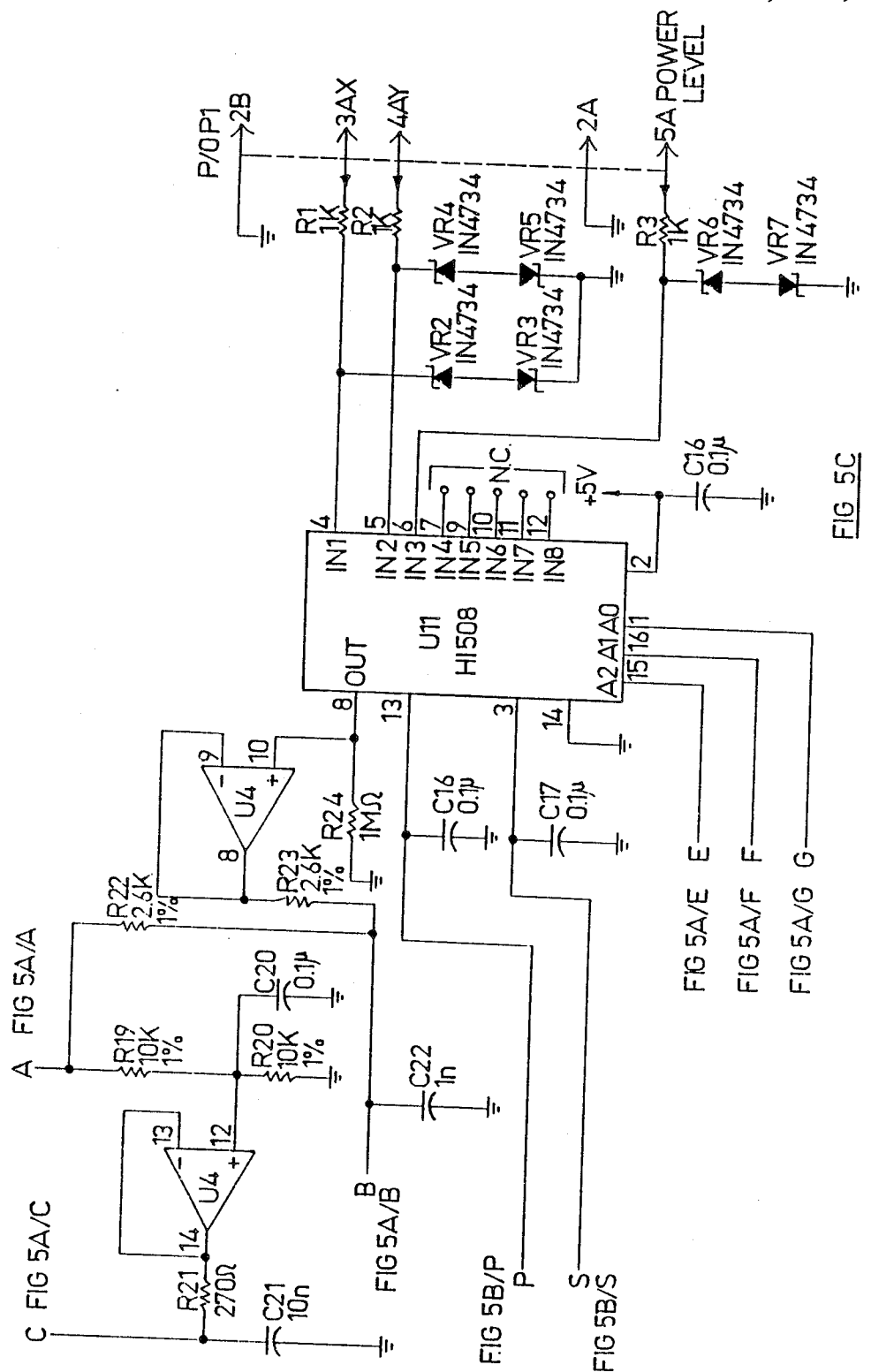
Figure 5D:
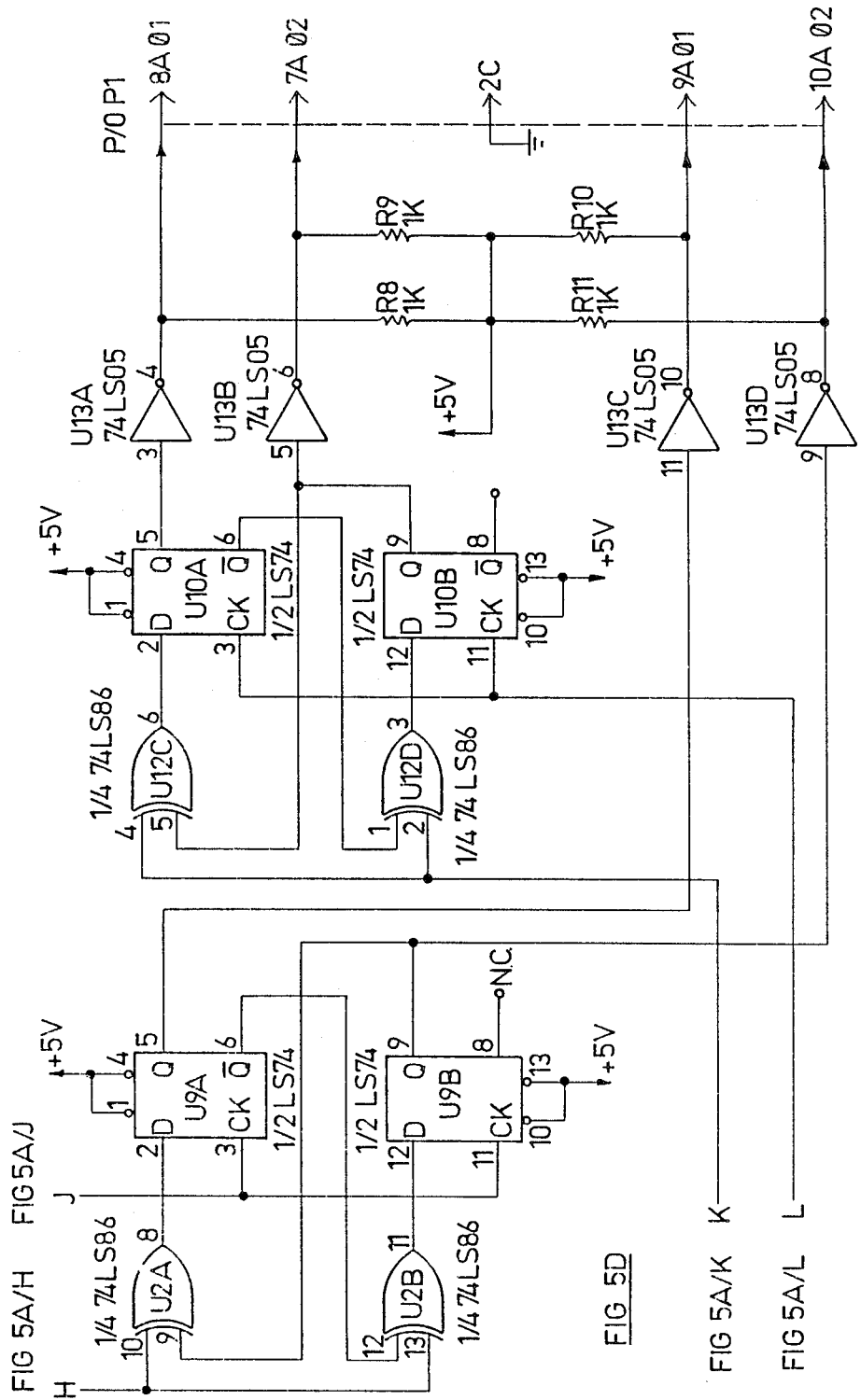

Reference is now made to FIG. 3 which provides a more detailed illustration of the capacitive matching apparatus of FIG. 2. The output from bi-directional coupler 50 is supplied to decoder 56, which includes a pair of series-connected amplifier pairs, each of which inputs to a splitter. The two splitters are 90 degrees out of phase and provide respective X and Y outputs. These two outputs, together with a power indication output, are supplied to computer controller 58. As noted above, the output of computer controller 58 is supplied to motor driver 60 which operates motors 62 and 64 of the matching unit 14.

Reference is now made to FIGS. 4A–4F, which are detailed schematic illustrations of the circuitry of decoder 56, each portion of the circuitry being indicated by a reference indication corresponding to the number of the corresponding drawings. For the sake of conciseness, it is deemed superfluous to describe verbally that which is clearly and completely shown in the schematic illustrations of FIGS. 4A–4F.

Controller 58, with the exception of its Z-80 CPU, is shown in detailed schematic form in FIGS. 5A–5D. For the sake of conciseness, it is deemed superfluous to describe verbally that which is clearly and completely shown in the schematic illustrations of FIGS. 5A–5D.

Figure 6B:
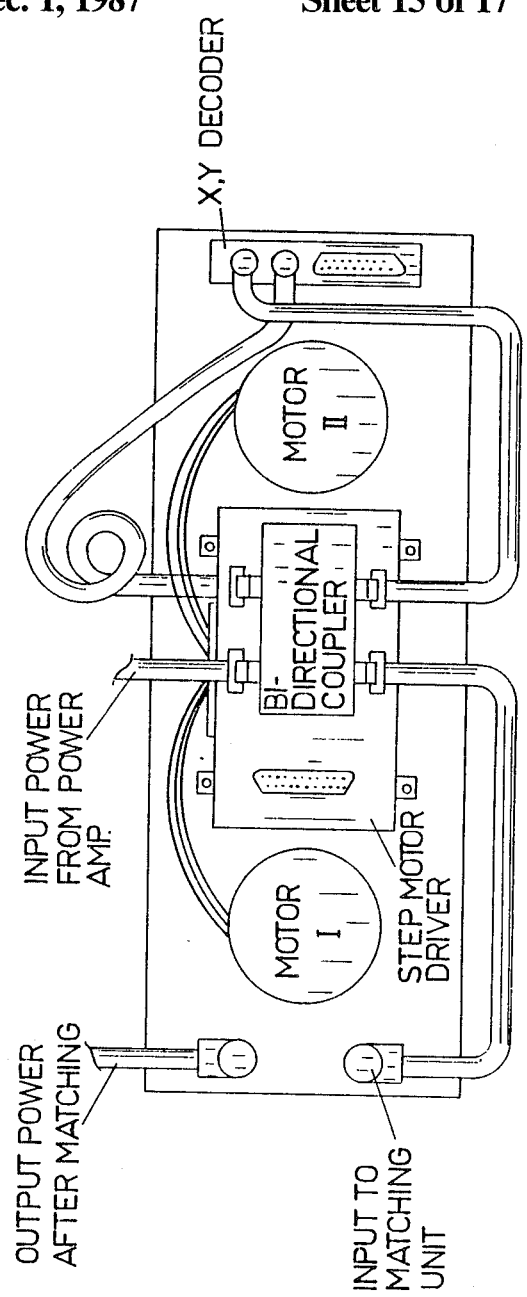

The matching unit 14 is illustrated pictorially in FIGS. 6A and 6B and is seen to correspond to the circuit diagram thereof in FIG. 3. Two multi-tapped inductors, L 1 and L 2, are each rated at 16 microhenries overall, and have individual portions rated as shown in FIG. 6A. Eight variable capacitors C, rated at 10–150 picofarads each, are arranged as shown, such that each motor controls four such variable compacitors independently of the other motor.

Figure 7A:
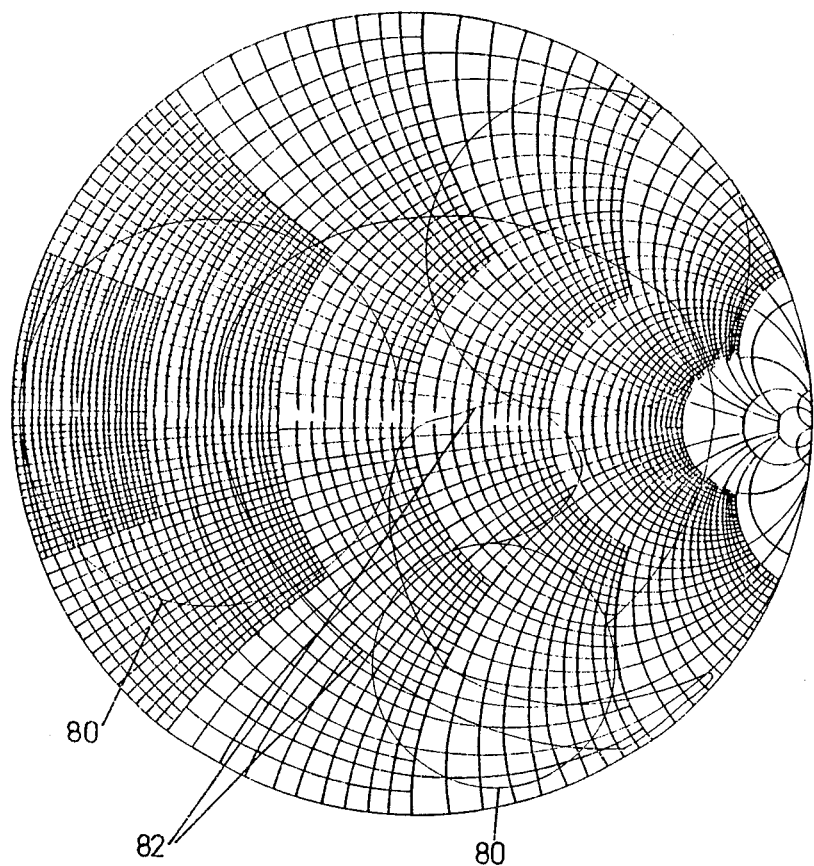
FIGS. 7A and 7B are two Smith charts having superimposed thereon traces indicating the operation of the matching unit of FIGS. 6A and 6B according to two alternative embodiments of the present invention.
Figure 7B:
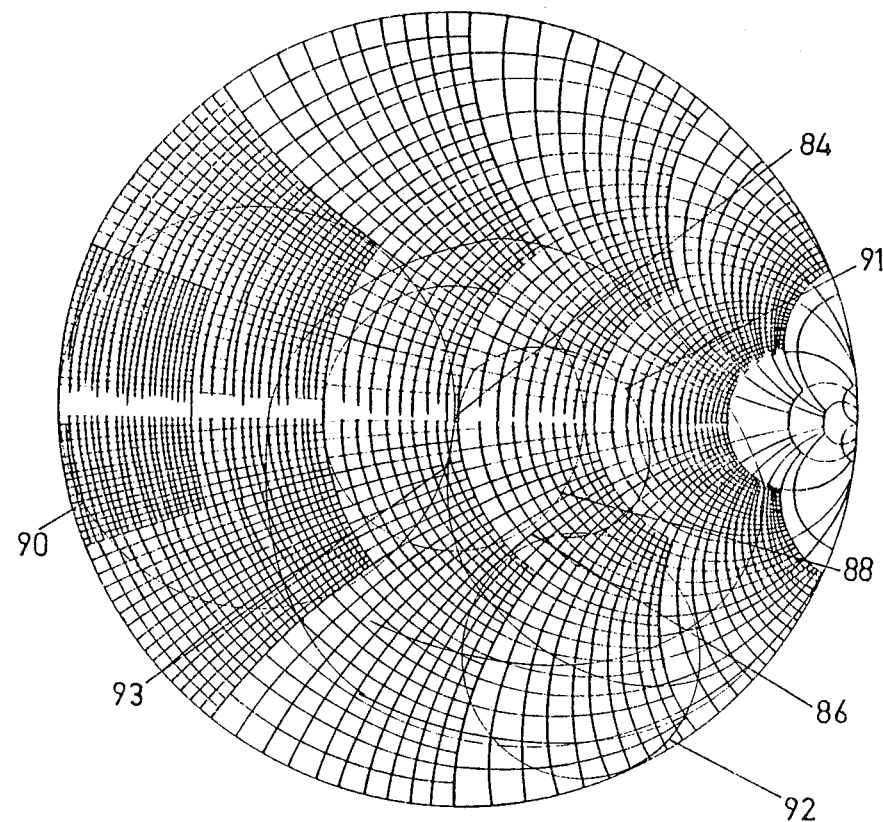

Reference is now made to FIGS. 7A and 7B which illustrate two Smith chart representations of the operation of the matching unit 14. The closed circular traces 80 indicate operation of one of the motors, such as motor 64, while the central, generally helical, trace 82 indicates the operation of the other motor, such as motor 62. The combined operation of the motors brings the reflected power to a desired minimum within a few seconds.

FIG. 7B is provided to illustrate the advantages of employing the x-y coordinate information representing the relationship between transmitted and reflected power according to the present invention, instead of merely considering the absolute values of transmitted and reflected power as in the prior art.

Location 84 represents the point of minimum reflected power. The reflected power increases with distance from location 84 in all directions. Accordingly circle 88 represents all of the points at which the reflected power is identical to that at a location 86.

The capacitive matching technique of the present invention will now be compared with the prior art technique for capacitive matching with reference to point 86. In accordance with the present invention, when the x and y vector components indicating the relationship between reflected and transmitted power are known, motor 62 is operated to change the impedance along the trace 91 until the impedance reaches the point closest to trace 90. When the impedance has reached trace 90, i.e. at point 93, the operation of motor 62 is terminated and motor 64 is then operated to vary the impedance along trace 90 until the impedance reaches location 84.

According to the prior art, each motor is operated individually in an effort to reach a local minimum of reflected power. This is an interative process which continues until the minimum reflected power is realized, and it can sometimes take a significant amount of time. This may be appeciated by considering that any movement along traces 88 and 92 from location 86 increases the reflected power, thus trapping the capacitive matching apparatus at a local minimum which is much higher than the minimum reflected power at location 84.

A computer listing of the software employed in controller 58 is appended hereto.

```
 1 errors: 00

10  ;************************
              20  ;         M.T.C
              30  ;
              40  ;
              50  ;    AUTOMATCH V2.0
              60  ;        25.02.86
              70  ; PROGRAMMER: HARRY
              80  ;
              90  ;THIS PROGRAM DOES THE
             100  ;AUTOMATIC MATCHING USING
             110  ;THE GEARED MATCH UNIT.
             120  ;
             130  ;THE MATCHING IS DONE IN
             140  ;TWO STAGES :
             150  ; 1.STATIC MODE-ROUGH
             160  ; 2.DYNAMIC MODE-FINE
             170  ;
             180  ; WORKS WITH AD0803
             190  ; ON THE PCB RF_IO
             200  ;
             210  ;************************
             220  ;
             230  ;
             240       ORG   #CE00
             250  ;
             260  ;
             270  ;
) C32ACE    280       JP    MOTOR1
: C348CE    290       JP    MOTOR2
, C384CE    300       JP    A_TO_D
) C3AECE    310       JP    MUL8
: C3BE0E    320       JP    CIRCLE
: C301CF    330       JP    SERIAL
: C3A2CF    340       JP    PARAL
: C377CF    350       JP    REFL_V
: C32CD0    360       JP    AUTOM
: C3BF01    370       JP    RD_XY
: C3D5D0    380       JP    KP_SER
! C33AD1    390       JP    KP_PAR
: C3E1D1    400       JP    KEEP
/ C30FD2    410       JP    MTC_ST
             420  ;
             430  ;_____
             440  ;
             450  ;PARALLEL MOTOR DRIVE
             460  ;SPEED CONTROL DONE WITH
             470  ;"MSPEED" WORD.
             480  ;_____
             490  ;
```

```
A ED4BD6E4      500 MOTOR1  LD    BC,(STEP1)
E 2109E4        510         LD    HL,SDIR1
1 3AD8E4        520         LD    A,(DIR1)
4 BE            530         CP    (HL)
5 2805          540         JR    Z,SAMED1
7 03            550         INC   BC
CE38 F60A       560         OR    %00001010
CE3A D37B       570         OUT   (123),A
                580 ;
CE3C ED43EAE4   590 SAMED1  LD    (PULSE1),BC
CE40 2AEAE4     600 WTM1    LD    HL,(PULSE1)
CE43 7C         610         LD    A,H
CE44 B5         620         OR    L
CE45 20F9       630         JR    NZ,WTM1
                640 ;
CE47 C9         650         RET
                660 ;
                670 ;
                680 ;----------------------
                690 ;
                700 ;SERIAL MOTOR DRIVE.
                710 ;SPEED CONTROL DONE WITH
                720 ;"MSPEED" WORD.
                730 ;----------------------
                740 ;
                750 ;
CE48 ED4BDAE4   760 MOTOR2  LD    BC,(STEP2)
CE4C 21DDE4     770         LD    HL,SDIR2
CE4F 3ADCE4     780         LD    A,(DIR2)
CE52 BE         790         CP    (HL)
CE53 2805       800         JR    Z,SAMED2
CE55 03         810         INC   BC
CE56 F60E       820         OR    %00001110
CE58 D37B       830         OUT   (123),A
                840 ;
CE5A ED43ECE4   850 SAMED2  LD    (PULSE2),BC
CE5E 2AECE4     860 WTM2    LD    HL,(PULSE2)
CE61 7C         870         LD    A,H
CE62 B5         880         OR    L
CE63 20F9       890         JR    NZ,WTM2
                900 ;
CE65 C9         910         RET
                920 ;
                930 ;
                940 ;----------------------
                950 ;
                960 ;ANALOG TO DIG. CONV.
                970 ;
                980 ;READS THE A_TO_D OUTPUT
                990 ;FROM THE CHANNEL HELD
               1000 ;IN "MUXCH" BYTE.(0-7)
               1010 ;CHANNEL 0-- X VALUE,
               1020 ;CHANNEL 1-- Y VALUE.
               1030 ;CHANNEL 2-- FWD.PWR.
               1040 ;CHANNEL 4-- TEST(D/A).
               1050 ;
               1060 ;----------------------
               1070 ;
               1080 *L+
               1090 ;
E503           1100 AD_FLG  EQU   #E503
E504           1110 ACTPWR  EQU   #E504
               1120 ;
CE66 F5        1130 AN_CON  PUSH  AF
CE67 DB7A      1140         IN    A,(122)
CE69 E6F0      1150         AND   #F0
CE6B 47        1160         LD    B,A
               1170 ;
               1180 ;
CE6C F1        1190         POP   AF
CE6D E607      1200         AND   7
CE6F B0        1210         OR    B
CE70 D37A      1220         OUT   (122),A
               1230 ;
```

```
CE72 060B      1240       LD    B,#0B
CE74 00        1250 NOPLP NOP
CE75 10FD      1260       DJNZ  NOPLP
               1270 ;
               1280 ;
CE77 AF        1290 CONV  XOR   A
CE78 D370      1300       OUT   (112),A
CE7A 00        1310       NOP
CE7B DB78      1320 CMV_TM IN   A,(120)
CE7D CB47      1330       BIT   0,A
CE7F 20FA      1340       JR    NZ,CMV_TM
               1350 ;
CE81 DB70      1360       IN    A,(112)
CE83 C9        1370       RET
               1380 ;
               1390 ;
               1400 ;
               1410 ;
CE84 F3        1420 A_TO_D DI
CE85 3A03E5    1430       LD    A,(AD_FLG)
CE88 A7        1440       AND   A
CE89 280C      1450       JR    Z,NOPWRD
               1460 ;
CE8B 3E02      1470       LD    A,2
CE8D CD66CE    1480       CALL  AN_CON
CE90 3204E5    1490       LD    (ACTPWR),A
CE93 AF        1500       XOR   A
CE94 3203E5    1510       LD    (AD_FLG),A
               1520 ;
CE97 3ADEE4    1530 NOPWRD LD   A,(MUXCH)
CE9A E607      1540       AND   7
CE9C 21EBE3    1550       LD    HL,SBIN+4
CE9F 0600      1560       LD    B,0
CEA1 4F        1570       LD    C,A
CEA2 09        1580       ADD   HL,BC
CEA3 E5        1590       PUSH  HL
CEA4 CD66CE    1600       CALL  AN_CON
CEA7 0600      1610       LD    B,0
CEA9 4F        1620       LD    C,A
CEAA E1        1630       POP   HL
CEAB 77        1640       LD    (HL),A
CEAC FB        1650       EI
CEAD C9        1660       RET
               1670 ;
               1680 ;
               1690 ;
               1700 ;
               1710 ;_____
               1720 ;
               1730 ;MULTIPLY ROUTINE
               1740 ;
               1750 ;MULTIPLIES A BY E AND
               1760 ;LEAVES RESULT IN HL&BC.
               1770 ;_____
               1780 ;
CEAE 1600      1790 MUL8  LD    D,0
CEB0 62        1800       LD    H,D
CEB1 6A        1810       LD    L,D
CEB2 0608      1820       LD    B,8
               1830 ;
CEB4 29        1840 MUL10 ADD   HL,HL
CEB5 07        1850       RLCA
CEB6 3001      1860       JR    NC,MUL20
CEB8 19        1870       ADD   HL,DE
               1880 ;
CEB9 10F9      1890 MUL20 DJNZ  MUL10
               1900 ;
CEBB 44        1910       LD    B,H
CEBC 4D        1920       LD    C,L
CEBD C9        1930       RET
               1940 ;
               1950 ;
               1960 ;
```

```
                1970 ;
                1980 ;
                1990 ;----------------------
                2000 ;
                2010 ;CIRCLE SUBROUTINE
                2020 ;
                2030 ;CALCULATES THE 50 OHMS
                2040 ;CIRCLE EQUATION USING
                2050 ;THE X&Y COORDINATES.
                2060 ;THE EQUATION FORM IS:
                2070 ;(X-64)^2+(Y-127)^2+64^2
                2080 ;----------------------
                2090 ;
                2100 ;
CEBE AF         2110 CIRCLE XOR  A
CEBF 32DEE4     2120        LD   (MUXCH),A
                2130 ;
CEC2 CD84CE     2140        CALL A_TO_D
                2150 ;
CEC5 5F         2160        LD   E,A
CEC6 CDAECE     2170        CALL MUL8
                2180 ;
CEC9 E5         2190        PUSH HL
                2200 ;
CECA 1E7F       2210        LD   E,#7F
CECC CDAECE     2220        CALL MUL8
CECF E1         2230        POP  HL
CED0 A7         2240        AND  A
CED1 ED42       2250        SBC  HL,BC
                2260 ;
CED3 E5         2270        PUSH HL
                2280 ;
CED4 3E01       2290        LD   A,1
CED6 32DEE4     2300        LD   (MUXCH),A
CED9 CD84CE     2310        CALL A_TO_D
                2320 ;
                2330 ;
CEDC 5F         2340        LD   E,A
CEDD CDAECE     2350        CALL MUL8
CEE0 E1         2360        POP  HL
CEE1 09         2370        ADD  HL,BC
                2380 ;
CEE2 E5         2390        PUSH HL
CEE3 1EFE       2400        LD   E,#FE
CEE5 CDAECE     2410        CALL MUL8
CEE8 E1         2420        POP  HL
CEE9 A7         2430        AND  A
CEEA ED42       2440        SBC  HL,BC
                2450 ;
CEEC 01013F     2460        LD   BC,16129
CEEF 09         2470        ADD  HL,BC
CEF0 CB7C       2480        BIT  7,H
CEF2 280A       2490        JR   Z,IS_POS
CEF4 7C         2500        LD   A,H
CEF5 2F         2510        CPL
CEF6 67         2520        LD   H,A
CEF7 7D         2530        LD   A,L
CEF8 2F         2540        CPL
CEF9 6F         2550        LD   L,A
CEFA 010100     2560        LD   BC,1
CEFD 09         2570        ADD  HL,BC
CEFE 4D         2580 IS_POS LD   C,L
CEFF 44         2590        LD   B,H
CF00 C9         2600        RET
                2610 ;
                2620 ;----------------------
                2630 ;
                2640 ;SERIAL MOVE ROUTINE
                2650 ;
                2660 ;MOVES THE SERIAL MOTOR
                2670 ;TRYING TO REACH THE
                2680 ;THE 50 OHMS CIRCLE.
                2690 ;----------------------
```

```
                2700 ;
0120            2710 FAST   EQU   288
0240            2720 SLOW   EQU   576
01F4            2730 SPCHNG EQU   500
                2740 ;
CF01 110100     2750 SERIAL LD    DE,1
CF04 ED53DAE4   2760        LD    (STEP2),DE
CF08 7B         2770        LD    A,E
CF09 32DCE4     2780        LD    (DIR2),A
CF0C 1B         2790        DEC   DE
CF0D ED53E2E4   2800        LD    (MEMSTP),DE
CF11 21FF7F     2810        LD    HL,#7FFF
CF14 22E4E4     2820        LD    (MINC),HL
CF17 013F06     2830        LD    BC,1599
                2840 ;
                2850 ;
CF1A D5         2860 FINDLP PUSH  DE
CF1B C5         2870        PUSH  BC
CF1C CDBECE     2880        CALL  CIRCLE
CF1F ED5BE0E4   2890        LD    DE,(DELTA)
CF23 EB         2900        EX    DE,HL
CF24 A7         2910        AND   A
CF25 ED52       2920        SBC   HL,DE
CF27 EB         2930        EX    DE,HL
CF28 3044       2940        JR    NC,F_EXIT
                2950 ;
CF2A 11F401     2960        LD    DE,SPCHNG
CF2D A7         2970        AND   A
CF2E ED52       2980        SBC   HL,DE
CF30 212001     2990        LD    HL,FAST
CF33 3003       3000        JR    NC,SAMESP
CF35 214002     3010        LD    HL,SLOW
CF38 22EEE4     3020 SAMESP LD    (MSPEED),HL
                3030 ;
                3040 ;
                3050 ;
CF3B CD48CE     3060        CALL  MOTOR2
CF3E CDBECE     3070        CALL  CIRCLE
CF41 ED5BE4E4   3080        LD    DE,(MINC)
CF45 A7         3090        AND   A
CF46 EB         3100        EX    DE,HL
CF47 ED52       3110        SBC   HL,DE
CF49 C1         3120        POP   BC
CF4A 380B       3130        JR    C,BIGGER
CF4C ED53E4E4   3140        LD    (MINC),DE
CF50 D1         3150        POP   DE
CF51 ED53E2E4   3160        LD    (MEMSTP),DE
CF55 1801       3170        JR    B_C
CF57 D1         3180 BIGGER POP   DE
CF58 13         3190 B_C    INC   DE
CF59 0B         3200        DEC   BC
CF5A 78         3210        LD    A,B
CF5B B1         3220        OR    C
CF5C 20BC       3230        JR    NZ,FINDLP
                3240 ;
CF5E 212001     3250        LD    HL,FAST
CF61 22EEE4     3260        LD    (MSPEED),HL
CF64 2AE2E4     3270        LD    HL,(MEMSTP)
CF67 22DAE4     3280        LD    (STEP2),HL
CF6A CD48CE     3290        CALL  MOTOR2
CF6D C9         3300        RET
                3310 ;
CF6E C1         3320 F_EXIT POP   BC
CF6F D1         3330        POP   DE
CF70 212001     3340        LD    HL,FAST
CF73 22EEE4     3350        LD    (MSPEED),HL
CF76 C9         3360        RET
                3370 ;
                3380 ;
                3390 ;
                3400 ;----------------------
                3410 ;
                3420 ;REFL.POWER SUBROUTINE
```

```
                3430 ;
                3440 ;CALCULATE MODUL OF REFL.
                3450 ;VECTOR.(X^2+Y^2)
                3460 ;------------------------
                3470 ;
CF77 AF         3480 REFL_V XOR  A
CF78 32DEE4     3490        LD   (MUXCH),A
                3500 ;
CF7B CD84CE     3510        CALL A_TO_D
CF7E D67F       3520        SUB  127
CF80 F285CF     3530        JP   P,X_POS
CF83 ED44       3540        NEG
CF85 5F         3550 X_POS  LD   E,A
CF86 CDAECE     3560        CALL MUL8
CF89 E5         3570        PUSH HL
                3580 ;
CF8A 3E01       3590        LD   A,1
CF8C 32DEE4     3600        LD   (MUXCH),A
CF8F CD84CE     3610        CALL A_TO_D
CF92 D67F       3620        SUB  127
CF94 F299CF     3630        JP   P,Y_POS
CF97 ED44       3640        NEG
CF99 5F         3650 Y_POS  LD   E,A
CF9A CDAECE     3660        CALL MUL8
CF9D D1         3670        POP  DE
CF9E 19         3680        ADD  HL,DE
                3690 ;
CF9F 4D         3700        LD   C,L
CFA0 44         3710        LD   B,H
CFA1 C9         3720        RET
                3730 ;
                3740 ;
                3750 ;
                3760 ;------------------------
                3770 ;
                3780 ;PARALLEL MOTOR MOVE
                3790 ;
                3800 ;MOVES THE PARALLEL MOTOR
                3810 ;TRYING TO REACH MINIMUM
                3820 ;REFLECTED VECTOR.
                3830 ;------------------------
                3840 ;
0240            3850 PSLOW  EQU  576
01F4            3860 SPCH_P EQU  500
                3870 ;
                3880 ;
CFA2 3E01       3890 PARAL  LD   A,1
CFA4 32D8E4     3900        LD   (DIR1),A
CFA7 110100     3910        LD   DE,1
CFAA ED53D6E4   3920        LD   (STEP1),DE
CFAE 1B         3930        DEC  DE
CFAF ED53E2E4   3940        LD   (MEMSTP),DE
CFB3 11FFFF     3950        LD   DE,#FFFF
CFB6 ED53E4E4   3960        LD   (MINC),DE
CFBA 013F06     3970        LD   BC,1599
CFBD DD210000   3980        LD   IX,0
                3990 ;
                4000 ;
                4010 ;
CFC1 C5         4020 OHM50  PUSH BC
CFC2 DDE5       4030        PUSH IX
CFC4 CD77CF     4040        CALL REFL_V
CFC7 ED5BE6E4   4050        LD   DE,(SDELTA)
CFCB EB         4060        EX   DE,HL
CFCC A7         4070        AND  A
CFCD ED52       4080        SBC  HL,DE
CFCF EB         4090        EX   DE,HL
CFD0 309C       4100        JR   NC,F_EXIT
                4110 ;
CFD2 11F401     4120        LD   DE,SPCH_P
CFD5 A7         4130        AND  A
CFD6 ED52       4140        SBC  HL,DE
CFD8 212001     4150        LD   HL,FAST
```

```
CFDB 3003        4160            JR    NC,SAME_P
CFDD 214002      4170            LD    HL,PSLOW
CFE0 22EEE4      4180 SAME_P LD         (MSPEED),HL
                 4190 ;
                 4200 ;
CFE3 CD2ACE      4210            CALL  MOTOR1
CFE6 3E01        4220            LD    A,1
CFE8 32DEE4      4230            LD    (MUXCH),A
CFEB CD84CE      4240            CALL  A_TO_D
CFEE CD1600      4250            CALL  SPTST
CFF1 FE87        4260            CP    135
CFF3 3010        4270            JR    NC,BIG1;LOOP
CFF5 FE77        4280            CP    119
CFF7 380C        4290            JR    C,BIG1;LOOP.
CFF9 AF          4300            XOR   A
CFFA 32DEE4      4310            LD    (MUXCH),A
CFFD CD84CE      4320            CALL  A_TO_D
D000 FE1E        4330            CP    30
D002 D26ECF      4340            JP    NC,F_EXIT
                 4350 ;
                 4360 ;
D005 DDE1        4370 BIG1       POP   IX
D007 DD23        4380 P_C        INC   IX
D009 C1          4390            POP   BC
D00A 0B          4400            DEC   BC
D00B 78          4410            LD    A,B
D00C B1          4420            OR    C
D00D 20B2        4430            JR    NZ,OHM50
                 4440 ;
D00F 212001      4450            LD    HL,FAST
D012 22EEE4      4460            LD    (MSPEED),HL
D015 C9          4470            RET
                 4480 ;
D016 FEC8        4490 SPTST      CP    200
D018 300B        4500            JR    NC,LETFST
D01A FE22        4510            CP    034
D01C 3807        4520            JR    C,LETFST
D01E 214002      4530            LD    HL,PSLOW
D021 22EEE4      4540            LD    (MSPEED),HL
D024 C9          4550            RET
D025 212001      4560 LETFST LD        HL,FAST
D028 22EEE4      4570            LD    (MSPEED),HL
D02B C9          4580            RET
                 4590 ;
                 4600 ;
                 4610 ;
                 4620 ;
                 4630 ;
                 4640 ;_____
                 4650 ;
                 4660 ;* AUTOMATCH START        *
                 4670 ;
                 4680 ;DOES THE STATIC MATCH AT
                 4690 ;LOW POWER.
                 4700 ;
                 4710 ;_____
                 4720 ;
D00A             4730 SHORT  EQU   10
E501             4740 MTCSTT EQU   #E501
                 4750 ;
D02C 00          4760 AUTOM  NOP
                 4770 ;
D02D 3E04        4780            LD    A,4
D02F 32F6E4      4790            LD    (AM_TRY),A
                 4800 ;
D032 212001      4810            LD    HL,FAST
D035 22EEE4      4820            LD    (MSPEED),HL
D038 AF          4830            XOR   A
D039 32DEE4      4840            LD    (MUXCH),A
D03C CD84CE      4850            CALL  A_TO_D
D03F FE0A        4860            CP    SHORT
D041 DC4600      4870            CALL  C,MV_SH
D044 1828        4880            JR    OKAUTO
```

```
                4890 ;
                4900 ;
D046 013F06     4910 MV_SH   LD      BC,1599
D049 210100     4920         LD      HL,1
D04C 22D6E4     4930         LD      (STEP1),HL
                4940 ;
D04F C5         4950 PSHORT  PUSH    BC
D050 CD2ACE     4960         CALL    MOTOR1
D053 AF         4970         XOR     A
D054 32DEE4     4980         LD      (MUXCH),A
D057 CD84CE     4990         CALL    A_TO_D
D05A C1         5000         POP     BC
D05B FE0A       5010         CP      SHORT
D05D D0         5020         RET     NC
                5030 ;
D05E CDAED0     5040         CALL    AMPTST
D061 3005       5050         JR      NC,SH_MAX
D063 2171D0     5060         LD      HL,CANTMT
D066 E3         5070         EX      (SP),HL
D067 C9         5080         RET
                5090 ;
D068 0B         5100 SH_MAX  DEC     BC
D069 78         5110         LD      A,B
D06A B1         5120         OR      C
D06B 20E2       5130         JR      NZ,PSHORT
D06D C9         5140         RET
                5150 ;
D06E CDAED0     5160 OKAUTO  CALL    AMPTST
D071 3E02       5170 CANTMT  LD      A,2
D073 3201E5     5180         LD      (MTCSTT),A
D076 D8         5190         RET     C
                5200 ;
D077 00         5210         NOP
D078 CD01CF     5220 OUTSH   CALL    SERIAL
D07B AF         5230         XOR     A
D07C 32DEE4     5240         LD      (MUXCH),A
D07F CD84CE     5250         CALL    A_TO_D
D082 FE0A       5260         CP      SHORT
D084 3005       5270         JR      NC,CONTP
D086 CD46D0     5280         CALL    MV_SH
D089 18ED       5290         JR      OUTSH
D08B CDA2CF     5300 CONTP   CALL    PARAL
D08E AF         5310         XOR     A
D08F 32DEE4     5320         LD      (MUXCH),A
D092 CD84CE     5330         CALL    A_TO_D
D095 FE87       5340         CP      135
D097 3009       5350         JR      NC,TS_LP
D099 FE77       5360         CP      119
D09B 3805       5370         JR      C,TS_LP
D09D AF         5380         XOR     A
D09E 3201E5     5390         LD      (MTCSTT),A
D0A1 C9         5400         RET
                5410 ;
D0A2 21F6E4     5420 TS_LP   LD      HL,AM_TRY
D0A5 35         5430         DEC     (HL)
D0A6 20C6       5440         JR      NZ,OKAUTO
D0A8 3E01       5450         LD      A,1
D0AA 3201E5     5460         LD      (MTCSTT),A
D0AD C9         5470         RET
                5480 ;
D0AE 08         5490 AMPTST  EX      AF,AF
D0AF 3AD5E4     5500         LD      A,(RF_STF)
D0B2 A7         5510         AND     A
D0B3 200A       5520         JR      NZ,AMPFLT
                5530 ;
D0B5 3A04E5     5540         LD      A,(ACTPWR)
D0B8 A7         5550         AND     A
D0B9 2804       5560         JR      Z,AMPFLT
                5570 ;
D0BB 08         5580         EX      AF,AF
D0BC 37         5590         SCF
D0BD 3F         5600         CCF
D0BE C9         5610         RET
```

```
                5620 ;
D0BF 08         5630 AMPFLT EX    AF,AF
D0C0 37         5640       SCF
D0C1 C9         5650       RET
                5660 ;
                5670 ;
                5680 ;
                5690 ;_____
                5700 ;
                5710 ;DELAY SOUBROUTINE.
                5720 ;
                5730 ;GENERATES A DELAY USING
                5740 ;THE TIME CONST.WORD,
                5750 ;"MSPEED".
                5760 ;_____
                5770 ;
D0C2 00         5780 MDELAY NOP
D0C3 D5         5790       PUSH  DE
D0C4 F5         5800       PUSH  AF
D0C5 ED5BEEE4   5810       LD    DE,(MSPEED)
                5820 ;
D0C9 1B         5830 MLP   DEC   DE
D0CA 00         5840       NOP
D0CB 00         5850       NOP
D0CC 00         5860       NOP
D0CD 7A         5870       LD    A,D
D0CE B3         5880       OR    E
D0CF 20F8       5890       JR    NZ,MLP
D0D1 F1         5900       POP   AF
D0D2 D1         5910       POP   DE
D0D3 00         5920       NOP
D0D4 C9         5930       RET
                5940 ;
                5950 ;_____
                5960 ;
                5970 ;DYNAMIC SERIAL MATCH.
                5980 ;
                5990 ;KEEPS MATCH.CLOSE TO
                6000 ;50 OHMS CIRCLE .
                6010 ;_____
                6020 ;
                6030 ;
0032            6040 HST   EQU   050
                6050 ;
D0D5 00         6060 KP_SER NOP
D0D6 CDBECE     6070       CALL  CIRCLE
D0D9 22F2E4     6080       LD    (TEMP2),HL
                6090 ;
D0DC 210100     6100       LD    HL,1
D0DF 22DAE4     6110       LD    (STEP2),HL
D0E2 212001     6120       LD    HL,FAST
D0E5 22EEE4     6130       LD    (MSPEED),HL
D0E8 AF         6140       XOR   A
D0E9 32DCE4     6150       LD    (DIR2),A
D0EC 32F5E4     6160       LD    (TRY2),A
                6170 ;
D0EF CDAED0     6180 KPS_LP CALL AMPTST
D0F2 D8         6190       RET   C
                6200 ;
                6210 ;
                6220 ;
D0F3 CD48CE     6230       CALL  MOTOR2
D0F6 CDBECE     6240       CALL  CIRCLE
D0F9 CD31D1     6250       CALL  TSTOKS
                6260 ;
D0FC 2AF2E4     6270       LD    HL,(TEMP2)
D0FF 113200     6280       LD    DE,HST
D102 19         6290       ADD   HL,DE
                6300 ;
D103 A7         6310       AND   A
D104 ED42       6320       SBC   HL,BC
D106 3806       6330       JR    C,EXDIR2
                6340 ;
```

```
D108 ED43F2E4  6350         LD    (TEMP2),BC
D10C 18E1      6360         JR    KPS_LP
               6370 ;
D10E 3ADCE4    6380 EXDIR2  LD    A,(DIR2)
D111 A7        6390         AND   A
D112 2806      6400         JR    Z,SETDIR
D114 AF        6410         XOR   A
D115 32DCE4    6420         LD    (DIR2),A
D118 1804      6430         JR    DIRCH
D11A 3C        6440 SETDIR  INC   A
D11B 32DCE4    6450         LD    (DIR2),A
               6460 ;
D11E CDBECE    6470 DIRCH   CALL  CIRCLE
D121 22F2E4    6480         LD    (TEMP2),HL
D124 CD48CE    6490         CALL  MOTOR2
D127 21F5E4    6500         LD    HL,TRY2
D12A 34        6510         INC   (HL)
D12B 7E        6520         LD    A,(HL)
D12C FE03      6530         CP    3
D12E D0        6540         RET   NC
               6550 ;
D12F 18BE      6560         JR    KPS_LP
               6570 ;
D131 115E01    6580 TSTOKS  LD    DE,350
D134 A7        6590         AND   A
D135 ED52      6600         SBC   HL,DE
D137 D0        6610         RET   NC
D138 E1        6620         POP   HL
D139 C9        6630         RET
               6640 ;
               6650 ;
               6660 ;
               6670 ;_____
               6680 ;
               6690 ;DYNAMIC PARAL.MATCH.
               6700 ;
               6710 ;KEEPS MATCH CLOSE TO
               6720 ;X-AXIS,Y=0.
               6730 ;_____
               6740 ;
               6750 ;
0001           6760 HST1    EQU   1
               6770 ;
D13A AF        6780 KP_PAR  XOR   A
D13B 32D8E4    6790         LD    (DIR1),A
D13E 32F4E4    6800         LD    (TRY1),A
D141 CDBFD1    6810         CALL  RD_XY
D144 0600      6820         LD    B,0
D146 ED43F0E4  6830         LD    (TEMP1),BC
               6840 ;
D14A CDAED0    6850 KPP_LP  CALL  AMPTST
D14D D8        6860         RET   C
               6870 ;
               6880 ;
D14E 79        6890         LD    A,C
D14F FE14      6900         CP    20
D151 3808      6910         JR    C,SL_F
D153 210100    6920         LD    HL,1
D156 112001    6930         LD    DE,FAST
D159 1806      6940         JR    SAVE_1
D15B 210100    6950 SL_F    LD    HL,1
D15E 114002    6960         LD    DE,SLOW
D161 2206E4    6970 SAVE_1  LD    (STEP1),HL
D164 ED53EEE4  6980         LD    (MSPEED),DE
               6990 ;
D168 CD2ACE    7000         CALL  MOTOR1
D16B CDBFD1    7010         CALL  RD_XY
D16E CDABD1    7020         CALL  TSTOKP
               7030 ;
D171 2AF0E4    7040         LD    HL,(TEMP1)
D174 110100    7050         LD    DE,HST1
D177 19        7060         ADD   HL,DE
               7070 ;
```

```
D178 A7          7080          AND   A
D179 0600        7090          LD    B,0
D17B ED42        7100          SBC   HL,BC
D17D 3806        7110          JR    C,EXDIR1
                 7120 ;
D17F ED43F0E4    7130          LD    (TEMP1),BC
D183 18C5        7140          JR    KPP_LP
                 7150 ;
D185 3AD8E4      7160 EXDIR1   LD    A,(DIR1)
D188 A7          7170          AND   A
D189 2806        7180          JR    Z,SETDR1
D18B AF          7190          XOR   A
D18C 32D8E4      7200          LD    (DIR1),A
D18F 1804        7210          JR    DIRCH1
D191 3C          7220 SETDR1   INC   A
D192 32D8E4      7230          LD    (DIR1),A
                 7240 ;
D195 CDBFD1      7250 DIRCH1   CALL  RD_XY
D198 0600        7260          LD    B,0
D19A ED43F0E4    7270          LD    (TEMP1),BC
D19E CD2ACE      7280          CALL  MOTOR1
D1A1 21F4E4      7290          LD    HL,TRY1
D1A4 34          7300          INC   (HL)
D1A5 7E          7310          LD    A,(HL)
D1A6 FE05        7320          CP    5
D1A8 D0          7330          RET   NC
D1A9 189F        7340          JR    KPP_LP
                 7350 ;
                 7360 ;
D1AB 78          7370 TSTOKP   LD    A,B
D1AC FE6E        7380          CP    110
D1AE 3809        7390          JR    C,NO_MV
D1B0 216400      7400          LD    HL,100
D1B3 22D6E4      7410          LD    (STEP1),HL
D1B6 CD2ACE      7420          CALL  MOTOR1
                 7430 ;
D1B9 79          7440 NO_MV    LD    A,C
D1BA FE05        7450          CP    5
D1BC D0          7460          RET   NC
D1BD E1          7470          POP   HL
D1BE C9          7480          RET
                 7490 ;
                 7500 ;
                 7510 ;
                 7520 ;_____
                 7530 ;
                 7540 ;READ X AND Y COORD.
                 7550 ;
                 7560 ;READS THE X&Y AND
                 7570 ;RETURNS IXI IN B,
                 7580 ;IYI IN C.(ABS.VALUES).
                 7590 ;_____
                 7600 ;
                 7610 ;
D1BF AF          7620 RD_XY    XOR   A
D1C0 32DEE4      7630          LD    (MUXCH),A
D1C3 CD84CE      7640          CALL  A_TO_D
D1C6 A7          7650          AND   A
D1C7 FACBD1      7660          JP    M,SX
D1CA 2F          7670          CPL
D1CB F5          7680 SX       PUSH  AF
D1CC 3E01        7690          LD    A,1
D1CE 32DEE4      7700          LD    (MUXCH),A
D1D1 CD84CE      7710          CALL  A_TO_D
D1D4 A7          7720          AND   A
D1D5 FAD9D1      7730          JP    M,SY
D1D8 2F          7740          CPL
D1D9 D67F        7750 SY       SUB   127
D1DB 4F          7760          LD    C,A
D1DC F1          7770          POP   AF
D1DD D67F        7780          SUB   127
D1DF 47          7790          LD    B,A
D1E0 C9          7800          RET
```

```
                  7810 ;
                  7820 ;
                  7830 ;_____
                  7840 ;
                  7850 ;DYNAMIC MATCH ROUTINE
                  7860 ;
                  7870 ;KEEPS THE BEST MATCH
                  7880 ;AT HIGH POWER.
                  7890 ;IF REFL.VECT IS OVER
                  7900 ;A MAX. VALUE THEN IT
                  7910 ;CALLS THE STATIC MATCH.
                  7920 ;_____
                  7930 ;
                  7940 ;
D1E1 00           7950 KEEP    NOP
D1E2 CDBECE       7960         CALL  CIRCLE
D1E5 117C01       7970         LD    DE,380
D1E8 A7           7980         AND   A
D1E9 ED52         7990         SBC   HL,DE
D1EB D4D500       8000         CALL  NC,KP_SER
                  8010 ;
D1EE CDBFD1       8020         CALL  RD_XY
D1F1 79           8030         LD    A,C
D1F2 FE07         8040         CP    7
D1F4 D43AD1       8050         CALL  NC,KP_PAR
                  8060 ;
D1F7 CD77CF       8070         CALL  REFL_V
D1FA 118403       8080         LD    DE,900
D1FD A7           8090         AND   A
D1FE ED52         8100         SBC   HL,DE
D200 D42CD0       8110         CALL  NC,AUTOM
D203 CD77CF       8120         CALL  REFL_V
D206 111801       8130         LD    DE,280
D209 A7           8140         AND   A
D20A ED52         8150         SBC   HL,DE
D20C D8           8160         RET   C
D20D 18D2         8170         JR    KEEP
                  8180 ;
                  8190 ;
                  8200 ;
                  8210 ;
                  8220 ;
                  8230 ;
                  8240 ;************************
                  8250 ;*                       *
                  8260 ;* HERE CALL FROM CTH.   *
                  8270 ;* TO TEST MATCH. AND    *
                  8280 ;* DO THE MATCH IF IS    *
                  8290 ;* NECESSARY.            *
                  8300 ;*                       *
                  8310 ;************************
DDF0              8320 PWRTBL EQU  #DDF0
0064              8330 D_TO_A EQU  #64
E3E7              8340 SBIN   EQU  #E3E7
E407              8350 CBIN   EQU  #E407
E4D5              8360 RF_STF EQU  #E4D5
E4D4              8370 RQ_PWR EQU  #E4D4
E500              8380 DTAPWR EQU  #E500
                  8390 ;
                  8400 ;
                  8410 ;
D20F 00           8420 MTC_ST NOP
D210 212C01       8430         LD   HL,300
D213 22E0E4       8440         LD   (DELTA),HL
D216 3E02         8450         LD   A,2
D218 32DFE4       8460         LD   (DELAY),A
D21B 21C800       8470         LD   HL,200
D21E 22E6E4       8480         LD   (SDELTA),HL
D221 215000       8490         LD   HL,80
D224 22E8E4       8500         LD   (STLIM),HL
D227 212001       8510         LD   HL,FAST
D22A 22EEE4       8520         LD   (MSPEED),HL
                  8530 ;
```

```
D220 2100E5      8540           LD     HL,DTAPWR
D230 3E14        8550           LD     A,20
D232 BE          8560           CP     (HL)
D233 301F        8570           JR     NC,DO_MAT
                 8580 ;
                 8590 ;
                 8600 ;
                 8610 ; Test reflected pwr :
                 8620 ;
D235 CD77CF      8630           CALL   REFL_V
D238 11C800      8640           LD     DE,200
D23B A7          8650           AND    A
D23C ED52        8660           SBC    HL,DE
D23E 3009        8670           JR     NC,TSTDYN
                 8680 ;
D240 3AD4E4      8690 SEND_P    LD     A,(RQ_PWR)
D243 D364        8700           OUT    (D_TO_A),A
D245 3200E5      8710           LD     (DTAPWR),A
D248 C9          8720           RET
                 8730 ;
                 8740 ;Fall here if refl.high :
                 9380 ;
                 9390 ;
E4D6 0000        9400 STEP1     DEFW   0
E4D8 00          9410 DIR1      DEFB   0
E4D9 00          9420 SDIR1     DEFB   0
E4DA 0000        9430 STEP2     DEFW   0
E4DC 00          9440 DIR2      DEFB   0
E4DD 00          9450 SDIR2     DEFB   0
E4DE 00          9460 MUXCH     DEFB   0
E4DF 02          9470 DELAY     DEFB   2
E4E0 5E01        9480 DELTA     DEFW   350
E4E2 0000        9490 MEMSTP    DEFW   0
E4E4 0000        9500 MINC      DEFW   0
E4E6 FA00        9510 SDELTA    DEFW   250
E4E8 5000        9520 STLIM     DEFW   80
E4EA 0000        9530 PULSE1    DEFW   0
E4EC 0000        9540 PULSE2    DEFW   0
E4EE 8001        9550 MSPEED    DEFW   #180
E4F0 0000        9560 TEMP1     DEFW   0
E4F2 0000        9570 TEMP2     DEFW   0
E4F4 00          9580 TRY1      DEFB   0
E4F5 00          9590 TRY2      DEFB   0
E4F6 00          9600 AM_TRY    DEFB   0
                 9610 ;
Pass 2 errors: 00

Table used:  1384  from  2500
                 8750 ;
D249 CD77CF      8760 TSTDYN    CALL   REFL_V
D24C 115802      8770           LD     DE,600
D24F A7          8780           AND    A
D250 ED52        8790           SBC    HL,DE
D252 3839        8800           JR     C,DO_DYN
                 8810 ;
D254 3E15        8820 DO_MAT    LD     A,21
D256 D364        8830           OUT    (D_TO_A),A
D258 3200E5      8840           LD     (DTAPWR),A
                 8850 ;
                 8860 ;Wait for power to stab.
                 8870 ;
D25B 3A04E5      8880 PWR_W     LD     A,(ACTPWR)
D25E FE0F        8890           CP     15
D260 D8          8900           RET    C
                 8910 ;
                 8920 ;
D261 DD21E7E3    8930           LD     IX,SBIN
D265 DDE5        8940           PUSH   IX
D267 DDCB01EE    8950           SET    5,(IX+1)
D26B DDCB00AE    8960           RES    5,(IX+0)
                 8970 ;
D26F CD2CD0      8980           CALL   AUTOM
```

```
D272 DDE1      8990          POP  IX
               9000 ;
D274 3A01E5    9010          LD   A,(MTCSTT)
D277 A7        9020          AND  A
D278 DDCB01AE  9030          RES  5,(IX+1)
D27C 28C2      9040          JR   Z,SEND_P
               9050 ;
D27E FE02      9060          CP   2
D280 2804      9070          JR   Z,PWRZRO
D282 DDCB00EE  9080          SET  5,(IX+0)
D286 AF        9090 PWRZRO   XOR  A
D287 D364      9100          OUT  (D_TO_A),A
D289 3200E5    9110          LD   (DTAPWR),A
D28C C9        9120          RET
               9130 ;
               9140 ;
D28D CDBECE    9150 DO_DYN   CALL CIRCLE
D290 11BE00    9160          LD   DE,190
D293 A7        9170          AND  A
D294 ED52      9180          SBC  HL,DE
D296 D4D500    9190          CALL NC,KP_SER
               9200 ;
D299 CDBFD1    9210          CALL RD_XY
D29C 79        9220          LD   A,C
D29D FE08      9230          CP   8
D29F D43AD1    9240          CALL NC,KP_PAR
               9250 ;
D2A2 189C      9260          JR   SEND_P
               9270 ;
               9280 *L+
D2A4 80        9290 LINK     DEFB #80
               9300 ;
               9310 ;          .
               9320 ;*********************
               9330 ;
               9340 ;VARS. DEFINITION:
               9350 ;
               9360 ;
E4D6           9370          ORG  #E4D6
```

It will be appreciated by persons skilled in the art that the present invention is not limited to what has been particularly shown and described hereinabove. Rather the scope of the present invention is defined only by the claims which follow:

I claim:

1. A hyperthermia apparatus, comprising:

power amplifier means for providing a variable output power;

remote electrode means for receiving said output power provided by said power amplifier means and for coupling said output power across a capacitive load interacting with said remote electrode means, said capacitive load constituting portions of a patient to be treated;

power transmission means for electrically applying said output power provided by said power amplifier means to the remote electrode means;

capacitive matching means including a capacitive matching unit and step motor means for providing real time capacitive matching between the power amplifier means and the capacitive load across the electrode means; and control means for governing the operation of the step motor means in accordance with real time sensing of reflected power from said electrode means, and wherein the control means comprises a bidirectional coupler, a decoder receiving an input from the bidirectional coupler and providing x and y coordinate indications of reflected power, and computer operated controller means for receiving the output of the decoder and providing operating instructions to the step motor means by means of Smith chart coordinates generated thereby, whereby the x and y coordinate indications provide direction indications to the step motor means to significantly reduce the real time required for capacitive matching.

2. The apparatus according to claim 1 wherein the capacitive matching means is operative for providing capacitive matching over a range of applied power extending from less than about 10 W to at least 1.2 KW.

* * * * *

UNITED STATES PATENT AND TRADEMARK OFFICE
CERTIFICATE OF CORRECTION

PATENT NO. : 4,709,701
DATED : Dec. 1, 1987
INVENTOR(S) : Raviv Weber

It is certified that error appears in the above-identified patent and that said Letters Patent is hereby corrected as shown below:

Column 3, lines 39-40 "pro-vide provide" should read --pro-vide--

Column 4, line 63 "compacitors" should read --capacitors--

Column 29, lines 22-48 "9380; ... Table used: 1384 from 2500" should be moved to appear in column 31 at end of printed computer listing immediately following the 39th program line, which reads "E406 9370 ORG #E4D6"

Signed and Sealed this

Twenty-third Day of May, 1989

Attest:

DONALD J. QUIGG

Attesting Officer

Commissioner of Patents and Trademarks